United States Patent
Cheng et al.

(10) Patent No.: US 6,597,931 B1
(45) Date of Patent: Jul. 22, 2003

(54) SYSTEM AND METHOD FOR ABSOLUTE OXYGEN SATURATION

(75) Inventors: Xuefeng Cheng, Milpitas, CA (US); Xiaorong Xu, Menlo Park, CA (US); Shuoming Zhou, Cupertino, CA (US); Lai Wang, Cupertino, CA (US)

(73) Assignee: Photonify Technologies, Inc., Sunnyvale, CA (US)

( * ) Notice: Subject to any disclaimer, the term of this patent is extended or adjusted under 35 U.S.C. 154(b) by 49 days.

(21) Appl. No.: 09/664,972

(22) Filed: Sep. 18, 2000

(51) Int. Cl.$^7$ .............................. A61B 5/00
(52) U.S. Cl. .................. 600/310; 600/322; 600/328
(58) Field of Search .................. 600/310, 322, 600/328, 336, 473, 475, 476; 356/39, 41; 250/339.01, 339.02, 339.05, 339.06, 339.11, 340, 341.1, 341.2

(56) References Cited

U.S. PATENT DOCUMENTS

| | | |
|---|---|---|
| 3,963,351 A | 6/1976 | Chance et al. |
| 5,119,815 A | 6/1992 | Chance |
| 5,167,230 A | 12/1992 | Chance |
| 5,402,778 A | 4/1995 | Chance |
| 5,564,417 A | 10/1996 | Chance |
| 5,596,987 A | 1/1997 | Chance |
| 5,664,574 A | 9/1997 | Chance |
| 5,676,143 A | 10/1997 | Simonsen et al. |
| 5,782,755 A | 7/1998 | Chance et al. |

(List continued on next page.)

OTHER PUBLICATIONS

Chance et al., "A Novel Method for Fast Imaging of Brain Function, Non–Invasively, with Light", *Optics Express*, vol. 2, No. 10, p. 411–423, (May 11, 1998).

(List continued on next page.)

*Primary Examiner*—Eric F. Winakur
(74) *Attorney, Agent, or Firm*—Ritter, Lang & Kaplan LLP

(57) ABSTRACT

The present invention generally relates to an apparatus and method for obtaining absolute values of concentrations of chromophores of a medium and/or absolute values of their ratios. More particularly, the present invention relates to non-invasive optical systems and methods for determining absolute values of oxygenated and/or deoxygenated hemoglobins and their ratios in a physiological medium. The optical system typically includes (1) a body, (2) a source module supported by the body, optically coupling with the medium, and irradiating into the medium multiple sets of electromagnetic waves with different wave characteristics, (3) a detector module supported by the body, optically coupling with the medium, and detecting such electromagnetic waves, and (4) a processing module operatively coupling with the detector module, and determining the absolute values of the concentrations and the ratios thereof from multiple wave equations applied to the source and detector modules. The processing module is designed to obtain such absolute values by a method typically including the steps of (1) obtaining multiple sets of wave equations, (2) eliminating source-dependent and detector-dependent parameters therefrom to obtain a set of intermediate equations, (3) providing a correlation of medium-dependent and geometry-dependent parameters with the chromophore concentrations or ratios thereof, (4) incorporating the correlation into the set of intermediate equations, and (5) obtaining the absolute values of the chromophore concentrations and ratios thereof.

53 Claims, 5 Drawing Sheets

U.S. PATENT DOCUMENTS

| | | | |
|---|---|---|---|
| 5,792,051 A | 8/1998 | Chance | |
| 5,803,909 A | 9/1998 | Maki et al. | 600/310 |
| 5,807,263 A | 9/1998 | Chance | |
| 5,820,558 A | 10/1998 | Chance | |
| 5,835,617 A | 11/1998 | Ohta et al. | |
| 5,853,370 A | 12/1998 | Chance et al. | |
| 5,865,754 A | 2/1999 | Sevick-Muraca et al. | |
| 5,899,865 A | 5/1999 | Chance | |
| 5,917,190 A | 6/1999 | Yodh et al. | |
| 5,954,053 A | 9/1999 | Chance et al. | |
| 5,987,346 A | 11/1999 | Benaron et al. | 600/407 |
| 5,987,351 A | 11/1999 | Chance | |
| 6,078,833 A * | 6/2000 | Hueber | 600/476 |
| 6,088,605 A | 7/2000 | Griffith et al. | 600/316 |
| 6,104,945 A | 8/2000 | Modell et al. | 600/473 |
| 6,151,518 A * | 11/2000 | Hayashi | 600/322 |

OTHER PUBLICATIONS

Fantini et al., "Non–Invasive Optical Mapping of the Piglet Brain in Real Time", *Optics Express*, vol. 4, No. 8, p. 308–314 (Apr. 12, 1999).

Wu et al., "Quantitative Detection of Hemoglobin Saturation on Piglet Brain by Near–Infrared Frequency–Domain Spectroscopy", *SPIE Photon Propagation in Tissues III*, vol. 3194, p. 55–62 (1997).

Siegel et al., "Diffuse Optical Tomography of Rat Brain Function", *SPIE Conference on Optical Tomography and Spectroscopy of Tissue III*, vol. 3597, p. 252–261, (Jan. 1999).

Cubeddu et al., "In Vivo Absorption and Scattering Spectra of Human Tissues in the Red and Near Infrared", *Advances in Optical Imaging and Photon Migration*, vol. 21, p. 271–274 (1998).

Ma et al., "Quantitative Study of Hypoxia Stress in Piglet Brain by IQ Phase Modulation Oximetry", *SPIE Conference on Optical Tomography and Spectroscopy of Tissue III*, vol. 3597, p. 642–649 (Jan. 1999).

Pogue et al., "Instrumentation and Design of a Frequency–Domain Diffuse Optical Tomography Imager for Breast Cancer Detection", *Optics Express*, vol. 1, No. 13, p. 391–403, (Dec. 1997).

\* cited by examiner

SYSTEM AND METHOD FOR ABSOLUTE OXYGEN SATURATION

FIELD OF THE INVENTION

The present invention generally relates to an apparatus and methods for determining absolute values of various properties of a physiological medium. In particular, the present invention relates to non-invasive optical systems and methods for determining absolute values of concentrations of oxygenated and deoxygenated hemoglobins (and/or their ratios) in the physiological medium. The present invention also relates to apparatus and methods for obtaining such absolute values by solving a generalized photon diffusion equation as well as its variations such as a modified Beer-Lambert equation.

BACKGROUND OF THE INVENTION

Near-infrared spectroscopy has been used for non-invasive measurement of various physiological properties in animal and human subjects. The basic principle underlying the near-infrared spectroscopy is that physiological tissues include various highly-scattering chromophores to the near-infrared waves with relatively low absorption. Many substances in a medium may interact or interfere with the near-infrared light waves propagating therethrough. Human tissues, e.g., include numerous chromophores such as oxygenated hemoglobin, deoxygenated hemoglobin, water, lipid, and cytochrome, where the hemoglobins are the dominant chromophores in the spectrum range of 700 nm to 900 nm. Accordingly, the near-infrared spectroscope has been applied to measure oxygen levels in the physiological medium such as tissue hemoglobin oxygen saturation and total hemoglobin concentrations.

Various techniques have been developed for the near-infrared spectroscopy, e.g., time-resolved spectroscopy (TRS), phase modulation spectroscopy (PMS), and continuous wave spectroscopy (CWS). In a homogeneous and semi-infinite model, both of TRS and PMS have been used to obtain spectra of an absorption coefficient and reduced scattering coefficient of the physiological medium by solving a photon diffusion equation, and to calculate concentrations of oxygenated and deoxygenated hemoglobins as well as tissue oxygen saturation. CWS has generally been designed to solve a modified Beer-Lambert equation and to measure changes in the concentrations of oxygenated and deoxygenated hemoglobins.

Despite their capability of providing the hemoglobin concentrations as well as the oxygen saturation, one major drawback of TRS and PMS is that the equipment is bulky and expensive. CWS may be manufactured at a lower cost but limited in its utility because it cannot compute the oxygen saturation from the changes in the concentrations of oxygenated and deoxygenated hemoglobins. Accordingly, there is a need for novel CWS systems and methods thereof for measuring absolute value of concentrations of the hemoglobins as well as the oxygen saturation in the physiological medium.

SUMMARY OF THE INVENTION

The present invention generally relates to an apparatus and method for obtaining absolute values of concentrations of chromophores of a medium and/or absolute values of their ratios. More particularly, the present invention relates to non-invasive optical systems and methods for determining absolute values of oxygenated and/or deoxygenated hemoglobins in a physiological medium.

In general, wave propagation or photon migration in a medium is described by a generalized diffusion equation:

$$I = \alpha \cdot \beta \cdot \gamma \cdot I_0 \cdot e^{[-B \cdot L \cdot \delta \cdot \Sigma_i (\epsilon_i C_i) + \sigma]} \tag{1}$$

where "$I_o$" is a variable representing an intensity of electromagnetic waves irradiated by a wave source and "I" is a variable for an intensity of electromagnetic waves detected by a wave detector. Parameter "α" is generally associated with the wave source and/or medium and accounts for, e.g., characteristics of the wave source such as power and configuration thereof, mode of optical coupling between the wave source and medium, and/or coupling loss therebetween. Parameter "β" is generally associated with the wave detector and/or medium and accounts for, e.g., characteristics of the wave detector, optical coupling mode between the wave detector and medium, and the associated coupling loss. Parameters "α" and "β" may also depend upon, to some extent, other system characteristics and optical properties of the medium, including those of chromophores included therein. Parameter "γ" may be either a proportionality constant (including, e.g., 1.0) or a system parameter which may change its value according to the characteristics of the wave source, wave detector, and/or medium. Parameter "B" generally accounts for lengths of optical paths of photons or electromagnetic waves through the medium, and is predominantly determined by the optical properties of the medium. However, an exact value of parameter "B" may also depend on the characteristics of the wave source and/or wave detector as well. A typical example of such parameter "B" is conventionally known as a path length factor. It is appreciated that the parameter "B" may also take the value of 1.0 where the generalized diffusion equation (1) is reduced to the Beer-Lambert equation. To the contrary, parameter "L" is generally geometry-dependent and accounts for a linear distance between the wave source and wave detector. Parameter "δ" may be either a proportionality constant (including, e.g., 1.0) or a system parameter which may be associated with the wave source, wave detector, and/or medium. Parameter "$\epsilon_i$" accounts for an optical interaction or interference of photons or electromagnetic waves with an i-th chromophore included in the medium. It is appreciated that, depending upon the definition and value of the parameter "δ", the parameter "$\epsilon_i$" may represent an extinction coefficient, an absorption coefficient, and/or a (reduced) scattering coefficient of the medium or the chromophores included therein. Variable "$C_i$" represents concentration of the i-th chromophore included the medium, and parameter "σ" is either a proportionality constant (including, e.g., 0.0) or a parameter which may be associated with the wave source, wave detector, and/or medium. Despite the numerous parameters of the generalized diffusion equation (1) and various modified versions thereof which will be described in greater detail below, the optical systems and methods of the present invention enable direct determination of absolute values of the chromophore concentrations and/or ratios thereof.

In one aspect of the present invention, a method is provided to solve a set of wave equations applied to an optical system having at least one wave source and at least one wave detector. Photons or electromagnetic waves are irradiated by the wave source, transmitted through the physiological medium including at least one chromophore, and detected by the wave detector. The wave equation, e.g., the generalized diffusion equation (1), expresses the intensity of electromagnetic waves detected by the wave detector (i.e., "I") as a function of system variables (e.g., "$I_o$" and "$C_i$") and system parameters (e.g., "$\alpha$," "$\beta$," "$\gamma$," "$B$," "$L$," "$\delta$," "$\epsilon_i$," and "$\sigma$"). The method generally includes the steps of obtaining multiple sets of equations by applying the wave equation to the optical system capable of irradiating multiple sets of electromagnetic waves having different wave characteristics, eliminating the source-dependent parameters (e.g., "$\alpha$") and detector-dependent parameter (e.g., "$\beta$") therefrom to obtain a set of intermediate equations, providing at least one correlation of the medium-dependent and geometry-dependent parameters (e.g., "B" and "L," respectively) with the chromophore concentrations (and/or their ratios), incorporating the correlation into the set of intermediate equations, and obtaining absolute values of the concentrations of the chromophores (and/or ratios thereof) based on the intensities of electromagnetic waves (e.g., "I" and "$I_o$") and the medium- or chromophore-dependent parameters (e.g., "$\epsilon_i$").

This embodiment of the present invention offers several benefits over the prior art. Contrary to the prior art CWS technology capable of measuring only the changes in the chromophore concentrations, the foregoing method of the present invention provides a direct means for assessing the "absolute values" of the chromophore concentrations as well as their ratios in various physiological media, e.g., tissues or cells in internal organs, muscles, and/or body fluids. The foregoing method of the present invention also allows physicians to make direct diagnosis of an "absolute property" of the physiological medium (i.e., compared with differential or relative values of the physiological properties obtainable by the prior art CWS technology). Furthermore, as will be described in detail below, the foregoing method of the present invention can be readily incorporated into conventional optical probes including any number of wave sources and detectors arranged in any arbitrary configurations. Therefore, the foregoing method allows construction of optical systems customized to specific clinical applications without compromising their performance characteristics.

Embodiments of this aspect of the present invention may include one or more of the following features.

The generalized diffusion equation (1) may be applied to an optical system with at least one wave source and at least one wave detector:

$$I_{mn} = \alpha_m \cdot \beta_n \cdot \gamma \cdot I_{0,m} \cdot e^{[-B_{mn} \cdot L_{mn} \cdot \delta \cdot \Sigma_i (\epsilon_i C_i) + \sigma]} \quad (2)$$

where the subscripts "m" and "n" represent an m-th wave source and an n-th wave detector, respectively.

The method may include the steps of applying equation (2) to the optical system to obtain a first and a second set of equations, eliminating at least one of $\alpha_m$, $\beta_n$, $\gamma$, $\delta$, and $\sigma$ from the first and second set of equations by performing mathematical operations thereon to obtain a third set of equations, providing at least one correlation which correlates the concentrations of the chromophores (or ratios thereof) with one or more terms of the third set of equations including $B_{mn}$ and/or $L_{mn}$, incorporating the above correlation into the third set of equations to replace such terms thereby, and obtaining an expression for absolute values of the concentrations of the chromophores (and/or ratios thereof) based on known or measured values of $I_{mn}$, $I_{o,m}$, and $\epsilon_i$.

The foregoing method may also include the steps of applying the optical system to the physiological medium including cells of organs, tissues, and body fluids, and measuring the absolute values of the chromophore concentrations (and/or their ratios) based on known or measured values of $I_{mn}$, $I_{o,m}$, and $\epsilon_i$. The measuring step may include an additional step of monitoring concentrations of oxy- or deoxy-hemoglobin, and/or a ratio thereof such as, e.g., (tissue) oxygen saturation.

The foregoing method may also include the step of determining presence of tumor cells in a finite area of the medium or determining a presence of an ischemic condition as well. In the alternative, the foregoing method may also include the steps of applying the optical system to the physiological medium including transplanted cells of organs and/or tissues and measuring absolute values of the chromophore concentrations (or their ratios) based on known or measured values of $I_{mn}$, $I_{o,m}$, and $\epsilon_i$. For example, the method may be applied to determine presence of an ischemic condition in the transplanted organs and tissues during or after surgical procedures.

The applying step of the foregoing method may include the step of irradiating the first and second set of electromagnetic waves having different wavelengths, phase angles, amplitudes, harmonics, and/or a combination thereof. For example, in the irradiating step, the first set of electromagnetic waves may have a first wavelength while the second set of electromagnetic waves may have a second wavelength which is different from the first wavelength.

The eliminating step of the foregoing method may include the step of deriving at least one first ratio of two wave equations both of which are selected from one of the first and second sets of the equations. The wave equations may be applied to the same wave source but to different wave detectors, thereby eliminating $\alpha_n$, $\gamma$, and $\sigma$ from the first ratio. Alternatively, the wave equations may be applied to two different wave sources but to the same wave detector, thereby eliminating $\beta_n$, $\gamma$, and $\sigma$ from the first ratio. The eliminating step may also include the step of deriving at least one second ratio of two wave equations both of which are selected from the other of the first and second sets of the equations. A sum of or a difference between the first and second ratios may also be obtained so as to eliminate at least one of $\alpha_m$ and $\beta_n$. In the alternative, the eliminating step may include the step of approximating both parameters "$\gamma$" and "$\delta$" as a unity.

The providing step of the foregoing method may include the step of providing a formula of the medium-dependent and geometry-dependent parameters as a polynomial, sinusoid or other functions of the chromophore concentrations (and/or ratios thereof). Such a formula may also include a zero-th order term. Alternatively, the medium-dependent and geometry-dependent parameters may be approximated as a constant.

In another aspect of the invention, an optical system is provided to determine the absolute values of the concentrations of chromophores in the physiological medium and/or ratios thereof. The optical system may include a body, a source module, a detector module, and a processing module. The source module is supported by the body and is arranged to optically couple with the medium so as to irradiate into the medium two or more sets of electromagnetic waves having different wave characteristics. The detector module is also supported by the body, and is arranged to optically couple with the medium and to detect electromagnetic waves transmitted through the medium. The processing module is also arranged to operatively couple with the detector module and configured to solve a set of wave equations such as equation (1) so that the absolute values of the concentrations of the chromophores (and/or their ratios)

can be directly determined. The processing module may be designed to operate at a TRS, PMS or CWS mode.

This embodiment of the present invention offers several benefits over the prior art near-infrared spectroscopy technologies such as TRS, PMS, and CWS. Compared with conventional TRS and PMS technologies, TRS and/or PMS optical systems of the present invention can be provided with better accuracy at a lower cost. Furthermore, the optical systems of the present invention operating at a CWS mode can measure the absolute values of the chromophore concentrations as well as their ratios, e.g., (tissue) oxygen saturation. Accordingly, various optical systems of the present invention can be manufactured as a low-cost and high-resolution hand-held device, bed-side monitoring device, and/or a portable device wearable by patients.

Embodiments of this aspect of the present invention may include one or more of the following features.

The wave source may be arranged to irradiate electromagnetic waves having different wavelengths, phase angles, amplitudes, harmonics or their combination. For example, the first set of the electromagnetic waves may have a first wavelength and a second set of said electromagnetic waves may have a second wavelength which is different from the first wavelength. Alternatively, the first set of electromagnetic waves may be carried by a first carrier wave and the second set of electromagnetic waves may be carried by a second carrier wave which has wave characteristics different from those of the first carrier wave, e.g., different wavelengths, phase angles, amplitudes, harmonics, and their combination.

The processing module may include an algorithm for determining the absolute values of the chromophore concentrations (or their ratios) based on various variables and/or parameters, e.g., the intensity of electromagnetic waves irradiated by the source module, intensity of electromagnetic waves detected by the detector module, and one or more system parameters accounting for interaction or interference of photons or electromagnetic waves with the medium.

The wave equations may include at least one term which is substantially dependent on the optical properties of the medium (i.e., medium-dependent) and/or configuration of the source and detector modules (i.e., geometry-dependent). Examples of such term may include, but not limited to "B" and "L" of equation (1) or "$B_{mn}$" and "$L_{mn}$" of equation (2). The algorithm of the processing module may include at least one correlation expressing a first function of the term as a second function of the chromophore concentrations (and/or ratios thereof). The second function may be any analytic function, e.g., a polynomial of the concentrations and/or ratios thereof. Alternatively, the algorithm may also be arranged to approximate the second function as a constant.

The source module may include at least one wave source and the detector module at least two wave detectors. Alternatively, the source module may include at least two wave sources while the detector module may include at least one wave detector. It is preferred, however, that both of the source and detector modules include, respectively, at least two wave sources and at least two wave detectors.

In one aspect of medical application of the present invention, the foregoing optical systems and methods therefor may be used to measure the absolute values of concentrations of oxygenated and deoxygenated hemoglobin and/or their ratio. Such optical systems will be beneficial in non-invasively diagnosing ischemic conditions and/or locating ischemia in various organs and tissues. For example, the optical system may be used to prognose or diagnose stroke, cardiac ischemia or other physiological abnormalities originating from or characterized by abnormally low concentration of oxy-hemoglobin. Accordingly, presence of cancerous tumors may be easily detected. The optical systems of the present invention may further be applied to cells disposed in epidermis, corium, and organs such as a lung, liver, and kidney.

In another aspect of medical application of the present invention, the foregoing optical systems and methods therefor may be applied to measure absolute values of the concentrations of oxy- as well as deoxy-hemoglobins to diagnose vascular occlusion during or after various surgical procedures including organ transplantation. In general, prognosis of organ transplantation depends on adequate supply of oxygenated blood to transplanted organs during and post surgical procedure. The optical system of the present invention may be used to detect vascular occlusion in transplanted heart, lung, liver, and kidney in its earliest stage.

In yet another aspect of medical application of the present invention, the foregoing optical systems and methods therefor may be applied to assess various absolute properties of the physiological medium. Examples of such conditions may include, but not limited to, concentrations (or their ratios) of lipids, cytochromes, water, and/or other chromophores in the medium.

The foregoing apparatus and methods of the invention may be employed for various applications, e.g., non-invasively disposed on the medium or, alternatively, to be invasively disposed on an internal medium. As used herein, the "chromophores" may mean any substances in a medium which exhibit at least minimum interaction with photons and/or electromagnetic waves transmitting or propagating therethrough. Examples of such chromophores may include, but not limited to, hemoglobins (e.g., deoxygenated or deoxy-hemoglobin (Hb) and oxygenated or oxy-hemoglobin (HbO)), cytochromes, lipids, water, enzymes, hormones, transmitters, proteins, cholesterols, apoproteins, carbohydrates, cytosomes, blood cells, cytosols, and other optically interacting materials present in the animal or human cells.

The terms "electromagnetic waves" include acoustic or sound waves, near-infrared rays, infrared rays, visible lights, ultraviolet rays, lasers, and/or rays of photons. Unless otherwise defined, all technical and scientific terms used herein have the same meaning as commonly understood and/or used by one of ordinary skill in the art to which this invention belongs. Although methods and materials similar or equivalent to those described herein can be applied and/or used in the practice of or testing the present invention, suitable methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1A:
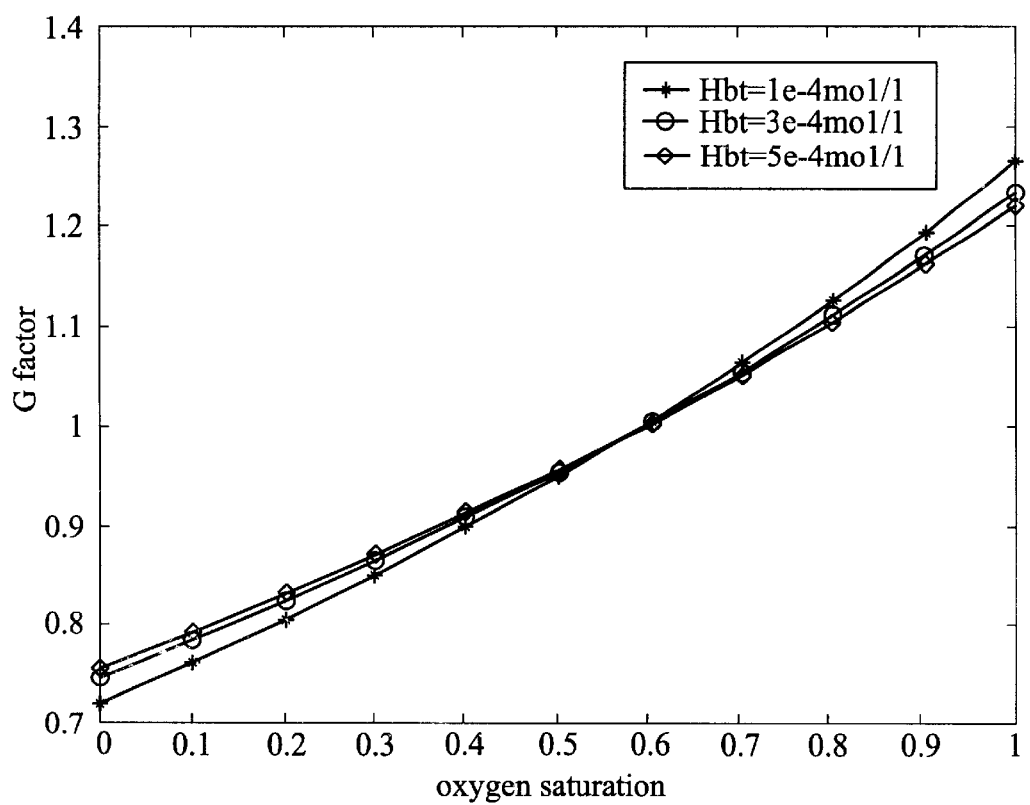
FIG. 1A is a plot of simulated values of G (i.e., a ratio of $F_1$ to $F_2$) at different wavelengths as a function of oxygen saturation according to the present invention.

The following description provides preferred embodiments of non-invasive optical systems and methods for determining absolute values of properties (or conditions) of physiological media. In particular, the description provides optical systems and methods of the present invention for determining the absolute values of concentrations of the hemoglobins (both of deoxy- and oxy-hemoglobin) and oxygen saturation (a ratio of oxy-hemoglobin concentration to total hemoglobin concentration which is a sum of the concentrations of oxy- and deoxy-hemoglobin) in the physiological media. The description further provides novel methods of solving a Beer-Lambert equation, a photon diffusion equations, and/or modified versions thereof.

In one aspect of the invention, a novel method is provided to solve the modified Beer-Lambert equation and/or the photon diffusion equation applied to an optical system including a source module and a detector module. The source and detector modules may include, respectively, at least one wave source and one wave detector. However, it is generally preferred that the source and detector modules include at least two wave sources and two wave detectors, respectively.

As described hereinabove, equation (1) is the generalized governing equation for describing migration of photons or propagation of electromagnetic waves in a medium:

$$I = \alpha \cdot \beta \cdot \gamma \cdot I_0 \cdot e^{\{-B \cdot L \cdot \delta \cdot \Sigma_i (\varepsilon_i C_i) + \sigma\}} \quad (1)$$

It is appreciated that the system parameters "$\gamma$" and "$\delta$" may have the value of 1.0 and "$\sigma$" may be 0.0. One simplified version of equation (1) may be obtained when the parameters "$\gamma$" and "$\delta$" are approximated as a unity:

$$I = \alpha \cdot \beta \cdot I_0 \cdot e^{\{-B \cdot L \cdot \Sigma_i (\varepsilon_i C_i) + \sigma\}} \quad (3a)$$

The conventional "photon diffusion equation" has the same form as equation (3a):

$$I = S \cdot D \cdot I_0 \cdot e^{\{-B \cdot L \cdot \Sigma_i (\varepsilon_i C_i) + A\}} \quad (3b)$$

where "S" corresponds to "$\alpha$" of equation (3a) and generally accounts for characteristics of the wave source such as power and configuration thereof, mode of optical coupling between the wave source and medium, and/or optical coupling loss therebetween, "D" corresponds to "$\beta$" of equation (3a) and generally accounts for characteristics of the wave detector, mode of optical coupling between the wave detector and medium, and/or the associated coupling loss, and "A" corresponds to "$\delta$" of equation (3a) which may be either a proportionality constant or a parameter associated with the wave source, wave detector, and/or medium.

For illustration purposes, an exemplary optical system may include, e.g., two wave sources (S1 and S2) each emitting electromagnetic waves of wavelength $\lambda_1$ and two wave detectors (D1 and D2) arranged to detect at least a portion of such electromagnetic waves. Applying the photon diffusion equation (3b) to each pair of the wave sources and detectors of the exemplary optical system yields the following set of equations:

$$I_{S1D1}^{\lambda_1} = I_{S1}^{\lambda_1} S_1 D_1 e^{-B_{S1D1} \left( \sum_i \varepsilon_i^{\lambda_1} C_i \right) L_{S1D1} + A} \quad (4a)$$

$$I_{S1D2}^{\lambda_1} = I_{S1}^{\lambda_1} S_1 D_2 e^{-B_{S1D2} \left( \sum_i \varepsilon_i^{\lambda_1} C_i \right) L_{S1D2} + A} \quad (4b)$$

$$I_{S2D1}^{\lambda_1} = I_{S2}^{\lambda_1} S_2 D_1 e^{-B_{S2D1} \left( \sum_i \varepsilon_i^{\lambda_1} C_i \right) L_{S2D1} + A} \quad (4c)$$

$$I_{S2D2}^{\lambda_1} = I_{S2}^{\lambda_1} S_2 D_2 e^{-B_{S2D2} \left( \sum_i \varepsilon_i^{\lambda_1} C_i \right) L_{S2D2} + A} \quad (4d)$$

where the superscript $\lambda_1$ denotes that various variables and parameters are obtained at the wavelength of $\lambda_1$.

A simple mathematical operation may eliminate at least one system parameter from the equations (4a) to (4d). For example, the source coupling factors such as $S_1$ and $S_2$ may be canceled therefrom by taking the first ratio of the equation (4a) to (4b) and by taking the fourth ratio of the equation (4d) to (4c). Logarithms of the first and second ratios are then taken to yield what are conventionally termed as "optical densities" (i.e., $OD_1^{\lambda_1}$ is defined as a logarithm of $I_{S1D1}^{\lambda_1} / I_{S1D2}^{\lambda_1}$ and $OD_2^{\lambda_2}$ defined as a logarithm of $I_{S2D2}^{\lambda_1} / I_{S2D1}^{\lambda_1}$). It is noted that these optical densities are generally insensitive to exact modes of optical coupling between the wave source and the physiological medium:

$$OD_1^{\lambda_1} = \ln \frac{I_{S1D1}^{\lambda_1}}{I_{S1D2}^{\lambda_1}} = \ln \frac{D_1}{D_2} + \left( B_{S1D2}^{\lambda_1} L_{S1D2} - B_{S1D1}^{\lambda_1} L_{S1D1} \right) \sum_i \varepsilon_i^{\lambda_1} C_i \quad (5a)$$

$$OD_2^{\lambda_1} = \ln \frac{I_{S2D2}^{\lambda_1}}{I_{S2D1}^{\lambda_1}} = \ln \frac{D_2}{D_1} + \left( B_{S2D1}^{\lambda_1} L_{S2D1} - B_{S2D2}^{\lambda_1} L_{S2D2} \right) \sum_i \varepsilon_i^{\lambda_1} C_i \quad (5b)$$

Other system parameters may also be eliminated through reformulating the above equations (5a) and (5b). For example, the terms including the detector coupling factors, $D_1$ and $D_2$, may be canceled by adding equation (5a) to (5b):

$$OD^{\lambda_1} = OD_1^{\lambda_1} + OD_2^{\lambda_2} = F^{\lambda_1} \sum_i \varepsilon_i^{\lambda_1} C_i \quad (6a)$$

where $$F^{\lambda_1} = (B_{S1D2}^{\lambda_1} L_{S1D2} - B_{S1D1}^{\lambda_1} L_{S1D1}) + (B_{S2D1}^{\lambda_1} L_{S2D1} - B_{S2D2}^{\lambda_1} L_{S2D2}) \quad (6b)$$

As manifest in the equation (6b), $F^{\lambda_1}$ is primarily determined by configurations of the wave sources and detectors (i.e., "L's" which are predominantly "geometry-dependent and which account for distances between each pair of a wave source and a wave detector) as well as the path length factors (i.e., "B's" which are predominantly "medium-dependent and which are determined by the optical properties of the physiological medium and/or electromagnetic waves).

Equations (6a) and (6b) may be applied to the physiological medium in order to obtain quantitative physiological information such as concentrations of the chromophores and/or their ratios. Numerous substances contained or suspended in the medium may be capable of interacting or interfering with photons or electromagnetic waves impinging or propagating therethrough. However, in many physiological media, hemoglobins such as deoxygenated and deoxy-hemoglobin (Hb) and oxygenated or oxy-hemoglobin (HbO) are the chromophores of the most physiological interests. Applying equations (6a) and (6b) to such physiological medium yields:

$$\frac{OD^{\lambda_1}}{F^{\lambda_1}} = \sum_i \varepsilon_i^{\lambda_1} C_i = \varepsilon_{Hb}^{\lambda_1}[HB] + \varepsilon_{HbO}^{\lambda_1}[HbO] \quad (7a)$$

where [Hb] and [HbO] respectively represent concentrations of Hb and HbO.

By arranging the wave sources, S1 and S2, or additional wave sources, e.g., S3 and S4, to irradiate a second set of electromagnetic waves having a wavelength $\lambda_2$ which is different from the wavelength $\lambda_1$, a companion equation of the equation (7a) is obtained as follows:

$$\frac{OD^{\lambda_2}}{F^{\lambda_2}} = \sum_i \varepsilon_i^{\lambda_2} C_i = \varepsilon_{Hb}^{\lambda_2}[Hb] + \varepsilon_{HbO}^{\lambda_2}[HbO] \quad (7b)$$

Accordingly, mathematical expressions of two system variables [Hb] and [HbO] can be readily derived from two algebraic system equations (7a) and (7b) as follows:

$$[Hb] = \frac{\varepsilon_{HbO}^{\lambda_2}\frac{OD^{\lambda_1}}{F^{\lambda_1}} - \varepsilon_{HbO}^{\lambda_1}\frac{OD^{\lambda_2}}{F^{\lambda_2}}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \quad (8a)$$

$$[HbO] = \frac{\varepsilon_{Hb}^{\lambda_1}\frac{OD^{\lambda_2}}{F^{\lambda_2}} - \varepsilon_{Hb}^{\lambda_2}\frac{OD^{\lambda_1}}{F^{\lambda_1}}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \quad (8b)$$

where $$F^{\lambda_1} = (B_{S1D2}{}^{\lambda_1} L_{S1D2} - B_{S1D1}{}^{\lambda_1} L_{S1D1}) + (B_{S2D1}{}^{\lambda_1} L_{S2D1} - B_{S2D2}{}^{\lambda_1} L_{S2D2}) \quad (8c)$$

and $$F^{\lambda_2} = (B_{S1D2}{}^{\lambda_2} L_{S1D2} - B_{S1D1}{}^{\lambda_2} L_{S1D1}) + (B_{S2D1}{}^{\lambda_2} L_{S2D1} - B_{S2D2}{}^{\lambda_2} L_{S2D2}) \quad (8d)$$

Expressions of other physiological properties, indices or variables may also be derived from the above equations. For example, oxygen saturation ($SO_2$) is a frequently used index for diagnosis of ischemic conditions and is generally defined as a ratio of concentration of oxy-hemoglobin to total concentration of hemoglobins (i.e., [HbT]=[Hb]+[HbO]):

$$SO_2 = \frac{[HbO]}{[HbT]} = \frac{[HbO]}{[Hb]+[HbO]} \quad (9a)$$

Incorporating equations (8a) and (8b) to equation (9a) yields a following formula for the oxygen saturation as a function of the extinction coefficients ($\varepsilon$'s), optical densities (OD's), and medium/geometry-dependent factors, $F^{\lambda_1}$ and $F^{\lambda_2}$:

$$SO_2 = \frac{\varepsilon_{Hb}^{\lambda_1}\frac{OD^{\lambda_2}}{OD^{\lambda_1}}\frac{F^{\lambda_1}}{F^{\lambda_2}} - \varepsilon_{Hb}^{\lambda_2}}{(\varepsilon_{Hb}^{\lambda_1} - \varepsilon_{HbO}^{\lambda_1})\frac{OD^{\lambda_2}}{OD^{\lambda_1}}\frac{F^{\lambda_1}}{F^{\lambda_2}} + (\varepsilon_{HbO}^{\lambda_2} - \varepsilon_{Hb}^{\lambda_2})} \quad (9b)$$

It is noted that the extinction coefficients of Hb and HbO at wavelengths $\lambda_1$ and $\lambda_2$ can be obtained experimentally or from the literature, and that the optical densities may be readily measured experimentally. However, estimation of $F^{\lambda_1}$ and $F^{\lambda_2}$ is not straight-forward because the path length factors including the terms $F^{\lambda_1}$ and $F^{\lambda_2}$ may depend on specific types of the physiological medium as well as optical or energy characteristics of photons or electromagnetic waves.

It is appreciated that the absolute value of [Hb], [HbO], and/or oxygen saturation may be obtained by estimating $F^{\lambda_1}$, $F^{\lambda_2}$ or their ratio as a function of, e.g., [Hb], [HbO], and/or oxygen saturation. For example, it may be assumed that $F^{\lambda_1}$, $F^{\lambda_2}$ or their ratio may only marginally depend on background optical properties and configurations of the wave sources and detectors. It is believed that these assumptions are fairly accurate in linear optical processes such as migration of photons or propagation of electromagnetic waves in the physiological media.

Once the correlations of the ratio of $F^{\lambda_1}$ to $F^{\lambda_2}$ with oxygen saturation is obtained for different physiological media by simply measuring the optical properties thereof, such correlations may be incorporated into equations (8a), (8b), and (9b), and the absolute values of [Hb], [HbO], and/or oxygen saturation may be obtained. In particular, a ratio of $F^{\lambda_1}$ to $F^{\lambda_2}$ may be approximated, e.g., as a polynomial of oxygen saturation as follows:

$$G = \frac{F^{\lambda_1}}{F^{\lambda_2}} = \sum_{j=0}^{\infty} a_j SO_2^j = a_0 + a_1 SO_2 + a_2 SO_2^2 + a_3 SO^3 + \ldots \quad (10)$$

where coefficients of each term (i.e., $\alpha_0, \alpha_1, \alpha_2, \alpha_3 \ldots$) may be obtained by, e.g., theoretical derivation, semi-theoretical estimation or numerical method best-fitting experimental data obtained between the values of G and oxygen saturation. By incorporating the formula for G of equation (10) into equation (9b), the absolute value of the oxygen saturation may be obtained from known values of the extinction coefficients (i.e., "$\varepsilon_i$'s") and experimentally measured optical densities (i.e., "OD's") as follows:

$$SO_2 = \frac{\varepsilon_{Hb}^{\lambda_1}\frac{OD^{\lambda_2}}{OD^{\lambda_1}}\sum_{j=0}^{\infty} a_j SO_2^j - \varepsilon_{Hb}^{\lambda_2}}{(\varepsilon_{Hb}^{\lambda_1} - \varepsilon_{HbO}^{\lambda_1})\frac{OD^{\lambda_2}}{OD^{\lambda_1}}\sum_{j=0}^{\infty} a_j SO_2^j + (\varepsilon_{HbO}^{\lambda_2} - \varepsilon_{Hb}^{\lambda_2})} \quad (11)$$

Equation (11) is generally solved numerically, but an analytical expression for the oxygen saturation may also be obtained when only a few first terms of the polynomials are adopted so as to approximate G, i.e., the ratio of $F^{\lambda_1}$ to $F^{\lambda_2}$. Other methods may also be applied to approximate G. For example, G may be estimated as a function of [Hb] and/or [HbO], although it is noted that the accuracy of this estimation may depend upon the one-to-one correspondence between G and [Hb] and/or [HbO]. Alternatively, G may be approximated as a constant as well. This approximation may be a reasonable assumption when $F^{\lambda_1}$ and $F^{\lambda_2}$ are relatively constant or tend to vary in proportion to each other according to different values of [Hb], [HbO], and/or oxygen saturation. In the alternative, the value of "$L_{mn}$" may be adjusted by manipulating geometric configuration of the wave sources and detectors so as to render G stay constant or vary in a pre-determined manner.

Similarly, each of $F^{\lambda_1}$ and $F^{\lambda_2}$ may be approximated as a function of [Hb], [HbO], and/or oxygen saturation. In the alternative, $F^{\lambda_1}$ and $F^{\lambda_2}$ may also be assigned specific values which may best approximate the optical system and/or the physiological medium of interest. By taking the simplest approach of approximating $F^{\lambda_1}$ and $F^{\lambda_2}$ to be a unity, the absolute values of [Hb], [HbO], and oxygen saturation may be obtained as follows:

$$[Hb] = \frac{\varepsilon_{HbO}^{\lambda_2} OD^{\lambda_1} - \varepsilon_{HbO}^{\lambda_1} OD^{\lambda_2}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \quad (12a)$$

$$[HbO] = \frac{\varepsilon_{Hb}^{\lambda_1} OD^{\lambda_2} - \varepsilon_{Hb}^{\lambda_2} OD^{\lambda_1}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \quad (12b)$$

$$SO_2 = \frac{\varepsilon_{Hb}^{\lambda_1}\frac{OD^{\lambda_2}}{OD^{\lambda_1}} - \varepsilon_{Hb}^{\lambda_2}}{(\varepsilon_{Hb}^{\lambda_1} - \varepsilon_{HbO}^{\lambda_1})\frac{OD^{\lambda_2}}{OD^{\lambda_1}} + (\varepsilon_{HbO}^{\lambda_2} - \varepsilon_{Hb}^{\lambda_2})} \quad (12c)$$

It is noted that [Hb], [HbO], and/or oxygen saturation obtained from the equations (12a) to (12c) (and/or other approximation methods described hereinabove) may be less accurate than those obtained from equations (8a), (8b), and (9b). Nevertheless, as long as the foregoing assumptions hold valid, one-to-one correlations may be expected between the true values of [Hb], [HbO], and oxygen saturation and those obtained from approximating equations (12a) to (12c). Such correlations may be determined once the optical properties of the physiological medium are known. For example, extinction coefficients, absorption coefficients, and/or scattering coefficients of the physiological medium (or those of the chromophores) may be determined for [HbT] and oxygen saturation. With known optical properties, oxygen saturation may be estimated at different levels of [HbT] through simulations of the diffusion equations and/or through experiments. Equations (12a) and (12b) may then be used to back-calculate [HbT], and a correction function can be calculated which correlates the calculated [HbT] with the true [HbT]. Similar or identical approach may be applied to calculate correction functions for [Hb] and/or [HbO] as well. It is noted that these methods may be applied to different physiological media (e.g., different human or animal subjects) to assess different optical properties and, therefore, to obtain different correction functions.

It is appreciated that the foregoing methods are applicable to any optical system and physiological media where migration of photons or propagation of electromagnetic waves may be reasonably described by the generalized governing equation (1). It should be noted that the parameter eliminating step of the foregoing methods may be applicable regardless of the specific numerical values assigned to the parameters "γ" and "δ". For example, γ can be eliminated by taking ratios of equation (4a) to (4b) and equation (4d) to (4c), and δ can be eliminated by taking the ratio of $F^{\lambda_1}$ to $F^{\lambda_2}$. In addition, the foregoing method may also be readily applicable to any modified versions of the governing equation (1) where the optical interaction or interference of the medium is described by absorption coefficient or scattering coefficients of the medium (or the chromophores included therein). For example, by assigning an adequate value and unit to parameter "γ," such modified equations can be converted into equations substantially similar or identical to the governing equation (1). Accordingly, it is manifest that the foregoing methods may be deemed universal methods for solving the generalized governing equation (1) for the chromophore concentrations and/or their ratios.

It is further appreciated that the absolute values of the chromophore concentrations (or their ratios) may be obtained by variations of the foregoing methods. For example, the detector coupling factors, $D_1$ and $D_2$, may first be eliminated from equations (4a) to (4d) by taking the third ratio of the equation (4a) to (4c) and the fourth ratio of the equation (4d) to (4b) as follows:

$$OD_3^{\lambda_1} = \quad (5c)$$

$$\ln\frac{I_{S1D1}^{\lambda_1}}{I_{S2D1}^{\lambda_1}} = \ln\frac{I_{S1}^{\lambda_1}}{I_{S2}^{\lambda_1}} + \ln\frac{S_1}{S_2} + (B_{S2D1}^{\lambda_1}L_{S2D1} - B_{S1D1}^{\lambda_1}L_{S1D1})\sum_i \varepsilon_i^{\lambda_1} C_i$$

$$OD_4^{\lambda_1} = \quad (5d)$$

$$\ln\frac{I_{S2D2}^{\lambda_1}}{I_{S1D2}^{\lambda_1}} = \ln\frac{I_{S2}^{\lambda_1}}{I_{S1}^{\lambda_1}} + \ln\frac{S_2}{S_1} + (B_{S1D2}^{\lambda_1}L_{S1D2} - B_{S2D2}^{\lambda_1}L_{S2D2})\sum_i \varepsilon_i^{\lambda_1} C_i$$

Similar to equations (5a) and (5b), this variational method yields optical densities $OD_3^{\lambda_1}$ and $OD_4^{\lambda_1}$ which are substantially insensitive the coupling mode between the wave detector and medium. By adding equation (5c) to (5d), the logarithmic ratios (i.e., one ratio of intensities of electromagnetic waves irradiated by the wave sources and the other ratio of the source coupling factors, $S_1$ and $S_2$) also cancel each other, yielding:

$$OD_{34}^{\lambda_1} = OD_3^{\lambda_1} + OD_4^{\lambda_1} = F_{34}^{\lambda_1}\sum_i \varepsilon_i^{\lambda_1} C_i \quad (6c)$$

where $$F_{34}^{\lambda_1} = (B_{S2D1}^{\lambda_1}L_{S2D1} - B_{S1D1}^{\lambda_1}L_{S1D1}) + (B_{S1D2}^{\lambda_1}L_{S1D2} - B_{S2D2}^{\lambda_1}L_{S2D2}). \quad (6d)$$

By applying equations (6c) and (6d) to the physiological medium including oxy- and deoxy-hemoglobins, following equation (7c) is obtained:

$$\frac{OD_{34}^{\lambda_1}}{F_{34}^{\lambda_1}} = \sum_i \varepsilon_i^{\lambda_1} C_i = \varepsilon_{Hb}^{\lambda_1}[Hb] + \varepsilon_{HbO}^{\lambda_1}[HbO] \quad (7c)$$

Similarly, a companion equation of equation (7c) may be obtained by applying the second set of electromagnetic waves having a wave length $\lambda_2$:

$$\frac{OD_{34}^{\lambda_2}}{F_{34}^{\lambda_2}} = \sum_i \varepsilon_i^{\lambda_2} C_i = \varepsilon_{Hb}^{\lambda_2}[Hb] + \varepsilon_{HbO}^{\lambda_2}[HbO] \quad (7d)$$

Accordingly, by solving equations (7c) and (7d), mathematical expressions of two system variables [Hb] and [HbO] can be obtained as follows:

$$[Hb] = \frac{\varepsilon_{HbO}^{\lambda_2}\frac{OD_{34}^{\lambda_1}}{F_{34}^{\lambda_1}} - \varepsilon_{HbO}^{\lambda_1}\frac{OD_{34}^{\lambda_2}}{F_{34}^{\lambda_2}}}{\varepsilon_{Hb}^{\lambda_1}\varepsilon_{HbO}^{\lambda_2} - \varepsilon_{Hb}^{\lambda_2}\varepsilon_{HbO}^{\lambda_1}} \quad (8e)$$

-continued $$[HbO] = \frac{\varepsilon_{Hb}^{\lambda_1} \frac{OD_{34}^{\lambda_2}}{F_{34}^{\lambda_2}} - \varepsilon_{Hb}^{\lambda_2} \frac{OD_{34}^{\lambda_1}}{F_{34}^{\lambda_1}}}{\varepsilon_{Hb}^{\lambda_1} \varepsilon_{HbO}^{\lambda_2} - \varepsilon_{Hb}^{\lambda_2} \varepsilon_{HbO}^{\lambda_1}} \quad (8f)$$

where $$F_{34}^{\lambda_1} = (B_{S2D1}{}^{\lambda_1}L_{S2D1} - B_{S1D1}{}^{\lambda_1}L_{S1D1}) + (B_{S1D2}{}^{\lambda_1}L_{S1D2} - B_{S2D2}{}^{\lambda_1}L_{S2D2}) \quad (8g)$$

and $$F_{34}^{\lambda_2} = (B_{S2D1}{}^{\lambda_2}L_{S2D1} - B_{S1D1}{}^{\lambda_2}L_{S1D1}) + (B_{S1D2}{}^{\lambda_2}L_{S1D2} - B_{S2D2}{}^{\lambda_2}L_{S2D2}) \quad (8h)$$

The oxygen saturation may then be expressed as:

$$SO_2 = \frac{\varepsilon_{Hb}^{\lambda_1} \frac{OD_{34}^{\lambda_2}}{OD_{34}^{\lambda_1}} \frac{F_{34}^{\lambda_1}}{F_{34}^{\lambda_2}} - \varepsilon_{Hb}^{\lambda_2}}{(\varepsilon_{Hb}^{\lambda_1} - \varepsilon_{HbO}^{\lambda_1}) \frac{OD_{34}^{\lambda_2}}{OD_{34}^{\lambda_1}} \frac{F_{34}^{\lambda_1}}{F_{34}^{\lambda_2}} + (\varepsilon_{HbO}^{\lambda_2} - \varepsilon_{Hb}^{\lambda_2})} \quad (9c)$$

Other variations of the foregoing methods leading to the equations (9b) and (9c) may also be used as long as they are designed to eliminate system parameters and to ultimately express [Hb], [HbO], and/or oxygen saturation in terms of known or measurable system variables or parameters such as, e.g., optical densities, extinction coefficients, and/or other geometry-dependent parameters.

It is further appreciated that the foregoing method of the present invention allows the wave sources to irradiate multiple sets of electromagnetic waves having different wave characteristics through various different embodiments. The simplest arrangement may be to provide two wave sources (such as S1 and S2), where each source is designated to irradiate electromagnetic waves having different wavelengths, phase angles, amplitudes, and/or harmonics. Alternatively, each wave source may also be arranged to irradiate substantially identical signal waves which are, however, superimposed on different carrier waves. In yet another alternative, a single or each wave source may be arranged to irradiate multiple sets of electromagnetic waves intermittently, sequentially or simultaneously as long as different sets of electromagnetic waves can be identifiable by one or more wave detectors. Similar arrangements may also be applied to the wave detectors as well. For example, two wave detectors (D1 and D2) may be provided where each detector is designated to detect only a single set of electromagnetic waves. Alternatively, a single or each wave detector may be arranged to detect multiple sets of electromagnetic waves with different wave characteristics on an intermittent, sequential or simultaneous mode. Because the foregoing methods of the present invention allow these various arrangements, the foregoing methods can be readily incorporated to any conventional spectroscopic techniques including, e.g., continuous wave spectroscopy, time resolved spectroscopy, and phase modulation spectroscopy.

In another aspect of the invention, an over-determined numerical method is provided to solve the modified Beer-Lambert equation and/or the photon diffusion equation applied to an optical system including a source module and a detector module, where at least one of the source module and detector module may be arranged to irradiate or detect more than two sets of electromagnetic waves. By arranging an optical system to provide "more equations" than "the number of system variables" of interest, resulting extra equations may be utilized for other purposes, e.g., (i) to enhance the accuracy of estimated values of system variables (e.g., chromophore concentrations or their ratios), (ii) to determine system parameters (e.g., "$\alpha_m$," "$\beta_n$," "$\gamma$," "$B_{mn}$," "$L_{mn}$," "$\delta$," "$\epsilon_i$," "$\sigma$" or other parameters such as absorption and scattering coefficients of the medium and/or chromophores) or (iii) to provide correlations of the medium- and/or geometry-dependent parameters of the equations (1) or (3b) with the system variable(s) and/or other system parameters.

In the first embodiment, the extra equations may be used to obtain multiple sets of the chromophore concentrations (and/or their ratios). It is expected that discrepancies may exist, at least to some extent, among the estimated values of the concentrations (and/or their ratios). Such discrepancies may be attributed to inherent idiosyncracies of each pair of the wave source and the wave detector. Alternatively, the discrepancies may also arise from a non-homogeneous medium, i.e., the medium having inherent variations in optical properties in different portions thereof. One way of taking advantage of different concentrations of the chromophores (and/or their ratios) may be to average such values to obtain an arithmetic, geometric or logarithmic average having reduced random or systematic errors and greater accuracy. Alternatively, each measured value may be weighted by an appropriate weight function which may account for, e.g., geometric configuration of the wave source-detector assembly.

In the second embodiment, correlations of the medium- and/or geometry-dependent parameters of the equations (1) or (3b) with, e.g., the chromophores concentrations (or their ratios) may be obtained from those extra equations. For example, when G (i.e., the ratio of $F^{\lambda_1}$ to $F^{\lambda_2}$) is approximated as a polynomial of oxygen saturation according to the equation (10), each of the coefficients of the polynomial may be assigned an initial value, and then improved by iterative techniques employing a conventional numerical fitting method. In addition, the extra equations may also be used to find the correction functions between approximated values of oxygen saturation, [Hb], and/or [HbO] and the true values thereof.

Furthermore, the extra equations may also be used to estimate system parameters (e.g., "$\alpha_m$," "$\beta_n$," "$\gamma$," "$B_{mn}$," "$L_{mn}$," "$\delta$," "$\epsilon_i$," "$\sigma$," and/or other system parameters such as absorption coefficients and/or scattering coefficients of the medium and/or chromophores). For example, a forward numerical scheme may be used to estimate absorption and reduced scattering coefficients of the physiological medium and/or chromophores included therein. As described hereinabove, migration of photons and propagation of electromagnetic waves in the medium can be described by the diffusion or transport equation. Assuming that the medium is semi-infinite and homogeneous, following equation may describe an intensity of electromagnetic waves detected by a j-th detector:

$$I_{ij}^{\lambda} = S_i^{\lambda} D_j^{\lambda} \phi(r_i, r_j, \mu_a, \mu_s) \quad (13)$$

where $S_i$ generally denotes a source coupling parameter accounting for, e.g., characteristics of an i-th wave source such as power and configuration thereof, mode of optical coupling between the i-th wave source and medium, and/or coupling loss therebetween, and $D_j$ is a detector coupling factor generally accounting for characteristics of a j-th wave detector, mode of optical coupling between the j-th wave detector and medium, and the associated coupling loss therebetween.

A symbol "$\phi$" represents a forward numerical model which simulates measurement for a given pair of the wave source and wave detector. Parameters "$\mu_a$" and "$\mu_s'$" represent, respectively, an absorption coefficient and reduced scattering coefficient. When the optical system includes, e.g., a total number of $N_S$ wave sources and $N_D$ wave detectors, equation (13) can be expressed in a matrix form as follows:

$$\begin{bmatrix} I_{11} & \cdots & I_{1,N_D} \\ \vdots & \ddots & \vdots \\ I_{N_S,1} & \cdots & I_{N_S,N_S} \end{bmatrix} = \begin{bmatrix} S_1^\lambda D_1^\lambda \phi(r_1, r_1, \mu_a, \mu_s') & \cdots & S_1^\lambda D_{N_D}^\lambda \phi(r_1, r_{N_D}, \mu_a, \mu_s') \\ \vdots & \ddots & \vdots \\ S_{N_S}^\lambda D_1^\lambda \phi(r_{N_S}, r_1, \mu_a, \mu_s') & \cdots & S_{N_S}^\lambda D_{N_D}^\lambda \phi(r_{N_S}, r_{N_D}, \mu_a, \mu_s') \end{bmatrix} \quad (14)$$

Each side of the equation (14) is divided by the first column of each matrix:

$$\begin{bmatrix} 1 & \cdots & \frac{I_{1,N_D}}{I_{1,1}} \\ \vdots & \ddots & \vdots \\ 1 & \cdots & \frac{I_{N_S,N_D}}{I_{N_S,1}} \end{bmatrix} = \begin{bmatrix} 1 & \cdots & \frac{D_{N_D}^\lambda \cdot \phi(r_1, r_1, \mu_a, \mu_s')}{D_1^\lambda \cdot \phi(r_1, r_1, \mu_a, \mu_s')} \\ \vdots & \ddots & \vdots \\ 1 & \cdots & \frac{D_{N_D}^\lambda \cdot \phi(r_{N_S}, r_{N_D}, \mu_a, \mu_s')}{D_1^\lambda \cdot \phi(r_{N_S}, r_1, \mu_a, \mu_s')} \end{bmatrix} \quad (15)$$

Each row of the matrices A and B of the equation (15) is then divided by the first row of each matrix:

$$A \equiv \begin{bmatrix} 1 & \cdots & 1 \\ \vdots & \ddots & \vdots \\ 1 & \cdots & \frac{I_{N_S,N_D}}{I_{N_S,1}} \end{bmatrix} \quad (16)$$

$$= \begin{bmatrix} 1 & \cdots & 1 \\ \vdots & \ddots & \vdots \\ 1 & \cdots & \frac{\phi(r_{N_S}, r_{N_D}, \mu_a, \mu_s') \cdot \phi(r_1, r_{N_D}, \mu_a, \mu_s')}{\phi(r_{N_S}, r_1, \mu_a, \mu_s') \cdot \phi(r_1, r_1, \mu_a, \mu_s')} \end{bmatrix}$$

$$\equiv B$$

As manifest in equation (16), both of the matrices A and B are functions of the absorption and reduced scattering coefficients and do not depend on the source- and detector-coupling parameters such as $S_i$ and $D_j$. Accordingly, by minimizing the difference between two matrices A and B (i.e., $\|A-B\|$), the best estimates of the absorption coefficient and the reduced scattering coefficient may be numerically obtained by conventional curve-fitting methods. After estimating the absorption and reduced scattering coefficients, [Hb], [HbO], and oxygen saturation may be obtained by the following set of formulae:

$$[Hb] = \frac{\varepsilon_{HbO}^{\lambda_2} \mu_a^{\lambda_1} - \varepsilon_{HbO}^{\lambda_1} \mu_a^{\lambda_2}}{\varepsilon_{Hb}^{\lambda_1} \varepsilon_{HbO}^{\lambda_2} - \varepsilon_{Hb}^{\lambda_2} \varepsilon_{HbO}^{\lambda_1}} \quad (17a)$$

$$[HbO] = \frac{\varepsilon_{Hb}^{\lambda_1} \mu_a^{\lambda_2} - \varepsilon_{Hb}^{\lambda_2} \mu_a^{\lambda_1}}{\varepsilon_{Hb}^{\lambda_1} \varepsilon_{HbO}^{\lambda_2} - \varepsilon_{Hb}^{\lambda_2} \varepsilon_{HbO}^{\lambda_1}} \quad (17b)$$

$$SO_2 = \frac{[HbO]}{[Hb]+[HbO]} = \frac{\varepsilon_{Hb}^{\lambda_1} \mu_a^{\lambda_2} - \varepsilon_{Hb}^{\lambda_2} \mu_a^{\lambda_1}}{\left(\varepsilon_{HbO}^{\lambda_2} \mu_a^{\lambda_1} - \varepsilon_{HbO}^{\lambda_1} \mu_a^{\lambda_2}\right) + \left(\varepsilon_{Hb}^{\lambda_1} \mu_a^{\lambda_2} - \varepsilon_{Hb}^{\lambda_2} \mu_a^{\lambda_1}\right)} \quad (17c)$$

It is noted that the foregoing over-determined method may be applied to the optical systems with at least two wave sources and three wave detectors, at least three wave sources and two wave detectors, or three wave sources and three wave detectors. Alternatively, the over-determined method may equally be applied to the optical systems where a single or each wave source or detector has the capability of irradiating or detecting multiple sets of electromagnetic waves, respectively.

It is appreciated that the foregoing over-determined method may be incorporated by any conventional numerical schemes. For example, a forward model, a backward model or a hybrid model may be applied to determine, e.g., an extinction coefficient, an absorption coefficient or a scattering coefficient of the physiological medium (or the chromophores included therein). Such models may also be applied to estimate the concentrations of the chromophores (and/or ratios thereof). It is noted, however, that the results obtained by such numerical models generally include inherent errors associated therewith. Such errors may be minimized by employing numerical models with the error terms of the second or higher order. However, such models may have a major drawback of requiring rigorous numerical computations. Accordingly, the accuracy and efficiency of each numerical model must be considered and compromised in selecting an appropriate one.

In yet another aspect of the invention, an optical system is provided to solve a set of wave equations and to determine absolute values of the concentrations of the chromophores (and/or ratios thereof) contained or suspended in a physiological medium. An exemplary optical system may include a body, a source module including at least one wave source, a detector module having at least one wave detector, and a processing module. The source module is supported by the body, and is generally arranged to optically couple with the physiological medium and to irradiate into the medium at least two sets of electromagnetic waves having different wave characteristics. The detector module is also supported by the body, and is arranged to optically couple with the medium and to detect electromagnetic waves transmitted through the medium. The processing module is arranged to operatively couple with the detector module, to solve a set of multiple wave equations, and to obtain the absolute values of the concentrations of chromophores and/or ratios thereof.

In general, the processing module includes an algorithm which is arranged to solve the foregoing equations (1) or (3b) or their modified versions. For example, one or more of the foregoing methods may be provided thereto as hardware or software or be implemented to a microprocessor so that the absolute values of the chromophore concentrations (and/or their ratios) may be calculated from, e.g., the intensity of electromagnetic waves irradiated by the source module (or its wave source(s)), intensity of electromagnetic waves detected by the detector module (or its wave detector(s)), and at least one system parameter which may account for an optical interaction and/or interference between the electromagnetic waves and the medium. The algorithm of the processing module may include one or more functions which correlates the medium- and/or geometry-dependent term(s) of the foregoing wave equations as a function of, e.g., the chromophore concentrations (or their ratios). The algorithm of the processing module may also be capable of executing the over-determined methods described hereinabove. In addition, the processing module and algorithm thereof may be arranged to operate on the TRS, PMS or CWS mode.

The source module may include at least one wave source and the detector module may include at least two wave detectors. Alternatively, the source module may include at least two wave sources while the detector module may include at least one wave detector. It is preferred, however, that the source and detector modules include, respectively, at least two wave sources and at least two wave detectors.

As described hereinabove, the foregoing methods of the present invention are rather insensitive to actual configuration of wave sources and detectors. Accordingly, the optical system of the present invention may include any number of wave sources and/or detectors arranged in any arbitrary configuration. However, a few source-detector configurations may be preferred so as to obtain the absolute values of the chromophore concentrations (and/or their ratios) with better accuracy, reliability, and reproducibility.

In the first preferred embodiment, multiple wave sources and/or detectors may be arranged so that near-distances between each wave source and detector pair are substantially identical. For example, for the source module including two (i.e., a first and second) wave sources and the detector module including two (i.e., a first and second) wave detectors, a distance (e.g., a near-distance) between the first wave source and the first wave detector may be arranged to be substantially similar to that (e.g., another near-distance) between the second wave source and the second wave detector. In addition, another distance (e.g., a far-distance) between the first wave source and the second wave detector may also be arranged to be substantially similar to that (e.g., another far-distance) between the second wave source and the first wave detector. It is appreciated that this embodiment is not necessarily required for every single pair of the wave source and detector. For example, when the source module has M wave sources and the detector module has N wave detectors (M and N are integers greater than 1), at least two of M wave sources and two of N wave detectors may be arranged so that a distance between an $M_1$-th wave source and an $N_1$-th detector is substantially similar to that between an $M_2$-th wave source and an $N_2$-th wave detector, and that a distance between the $M_1$-th wave source and the $N_2$-th wave detector is substantially similar to that between the $M_2$-th wave source and the $N_1$-th wave detector, where $M_1$ and $M_2$ are both integers between 1 and M, and $N_1$ and $N_2$ are both integers between 1 and N.

In the second preferred embodiment, wave detectors may be arranged substantially linearly along a straight line. As will be demonstrated in Examples, this arrangement has produced the concentrations of oxygenated and deoxygenated hemoglobins and oxygen saturation with great accuracies. It is noted that not all wave detectors have to be arranged linearly. For example, a substantial portion of the wave detectors may only have to be disposed substantially along the straight line. In this embodiment, it is also preferred that at least one wave source be disposed on one side of the straight line while at least one other wave source be disposed on the other side of the straight line.

In operation, a source module with at least one wave source and a detector module having at least one wave detector are provided to an active surface of an optical probe which is operatively connected with a main body of an optical system. Alternatively, the wave source and/or detector modules may be disposed at the main body and optical fibers may be provided to connect the source and detector modules to openings provided on the active surface of the optical probe. Any conventional wave sources and detectors may be used for such optical prove. It is preferred, however, that the wave source is capable of irradiating electromagnetic waves in the near-infrared range, e.g., between 500 and 1,200 nm or, in particular, between 600 and 900 nm, and that the wave detector has appropriate sensitivity to such electromagnetic waves. The optical probe is placed on a physiological medium, with its active surface disposed on the medium to form an optical coupling therebetween. The source module is activated so that at least two sets of electromagnetic waves having different wave characteristics are irradiated into the medium. The detector module then picks up different sets of electromagnetic waves irradiated by the wave source, propagated through the medium, and directed toward the wave detector. The wave detector generates electric signals which are received by the processing module of the main body of the optical system. Based on the optical densities and at least one system parameter such as extinction coefficients of the chromophores, the processing module computes the absolute values of the oxygenated hemoglobin concentration, the deoxygenated hemoglobin concentration or the oxygen saturation.

It is noted that the optical system according to the present invention may include an equation solving module which is operationally separate from the processing module. Such an equation solving module may include variety of numerical models designed perform one or more of the foregoing methods of the present invention.

Although the foregoing disclosure has been directed toward obtaining the absolute values of the concentrations of oxygenated and deoxygenated hemoglobins (and/or their ratios), the foregoing optical systems and methods therefor may be applicable to obtain absolute values of other substances in the medium or properties thereof. For example, similar or identical systems and methods may be used to determine the absolute values of concentrations (or their ratios) of other chromophores such as lipids, cytochromes, water, and the like. Depending upon the absorption or scattering characteristics, the wavelengths of the electromagnetic waves may be adjusted for better resolution. In addition, chemical compositions may be added to the medium to enhance optical interaction or interference of chromophores in the medium or to convert an non-chromatic substance of the medium into a chromophore.

As described hereinabove, the foregoing optical systems and methods of the present invention are preferred to be incorporated to the continuous wave spectroscopic technology. However, such systems and methods may readily be incorporated into the time-resolved and phase-modulation spectroscopic technologies as well.

The optical systems and methods according to the present invention find a variety of medical applications. As described hereinabove, such optical systems and methods may be applied to measure the absolute values of concentrations of oxygenated and deoxygenated hemoglobin and/or their ratio. Such optical systems will be beneficial in non-invasively diagnosing ischemic conditions and/or locating ischemia in various organs and tissues such as, e.g., a brain (stroke), heart (ischemia) or other physiological abnormalities originating from or characterized by abnormally low concentration of oxy-hemoglobin. In addition, presence of cancerous tumors in various internal organs, breasts, and skins may be easily detected as well. Such optical systems and methods may further be applied to cells disposed in epidermis, corium, and organs such as a lung, liver, and kidney. Such optical systems and methods may also be applied to diagnose vascular occlusion during or after surgical procedures including transplantation of tissues, skins, and organs, e.g., heart, lung, liver, and kidney.

Following examples describe simulation and experimental results obtained by the optical systems and methods thereof according to the present invention. All simulation and experimental results indicate that the optical systems and methods thereof provide accurate predictions of the concentrations of the hemoglobins as well as the oxygen saturation.

EXAMPLE 1

The diffusion equation (3b) was numerically solved for optical proves with multiple wave sources and detectors arranged in various configurations. The equations were applied to a sample physiological medium such as a semi-infinite, homogeneous diffuse medium with different background optical properties. Diffuse reflectances were calculated according to an imaging source approach disclosed in an article entitled, "Boundary conditions for the diffusion equation in radiative transfer" by R. C. Haskell et al. and published in Journal of Optical Society of America (11, p. 2727–2741, 1994). Values of G (the ratio of $F^{\lambda_1}$ to $F^{\lambda_2}$) were estimated at different levels of oxygen saturation and fitted as a polynomial thereof.

Figure 1B:
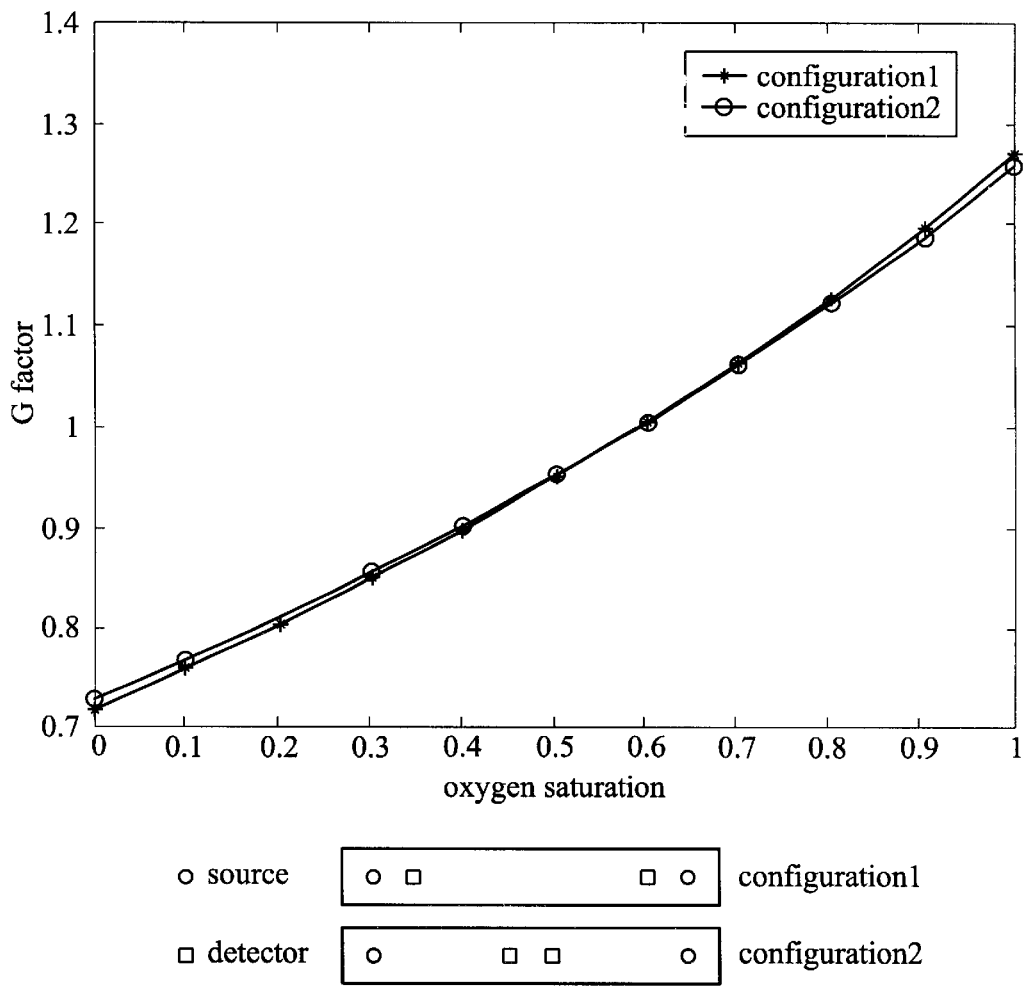
FIG. 1B is another plot of simulated values of G at different wavelengths as a function of oxygen saturation according to the present invention.
Figure 1C:
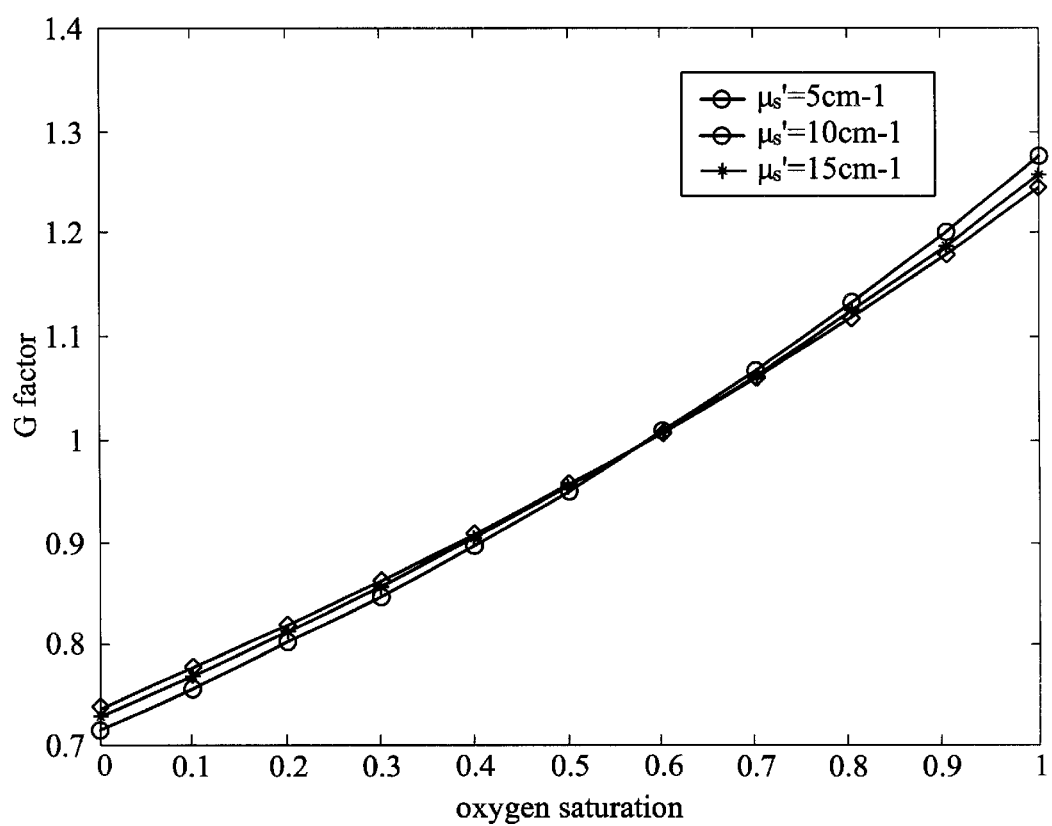
FIG. 1C is yet another plot of simulated values of G at different wavelengths as a function of oxygen saturation according to the present invention.

FIGS. 1A to 1C are plots of G's (ratios of F's simulated at different wavelengths) as a function of oxygen saturation. As shown in the figures, all simulation results showed distinct one-to-one correlations between G and oxygen saturation, and that the dependence of G on oxygen saturation was substantially insensitive to the source-detector configuration as well as the background optical properties. Conventional curve-fitting methods, such as the least-squares method, were applied to numerically estimate the coefficients of equation (10) (i.e., $\alpha_0, \alpha_1, \alpha_2, \alpha_3 \ldots$). For example, in a system with background reduced scattering coefficient of 10 cm$^{-1}$ and the total hemoglobin concentration of 10$^{-4}$ mol/liter and simulated with electromagnetic waves having wavelengths of 780 nm and 830 nm, following equation approximated the relation between G and oxygen saturation:

$$G = \frac{F^{\lambda_1}}{F^{\lambda_2}} = 0.728 + 0.399 \cdot SO_2 + 0.064 \cdot SO_2^2 + 0.067 \cdot SO_2^3 \tag{18}$$

EXAMPLE 2

Figure 2:
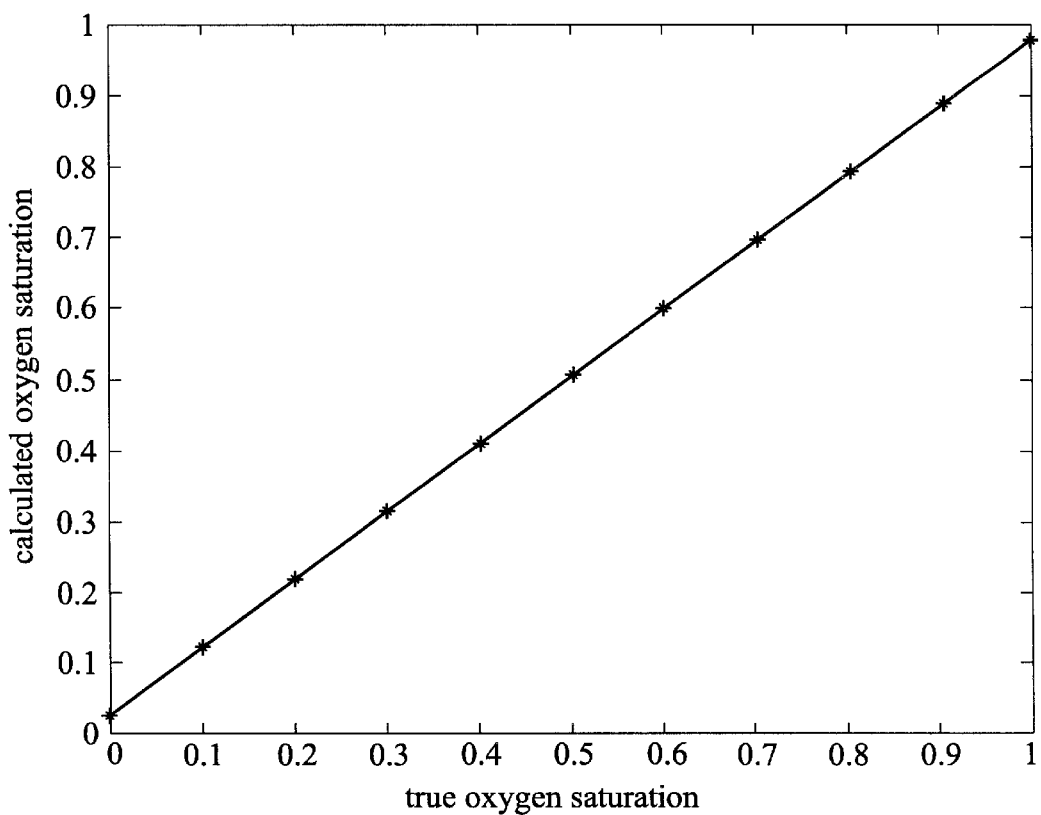
FIG. 2 is another plot of calculated oxygen concentration versus true oxygen saturation in a medium with a different background scattering coefficient and total hemoglobin concentration according to the present invention.

Further simulations were performed in a system with the background scattering of 7 cm$^{-1}$ and the total hemoglobin concentration of 2×10$^{-4}$ mol/liter. In the simulations, $SO_2$ was varied from 0 to 100%. FIG. 2 is a plot of calculated oxygen saturation contrasted against true oxygen saturation. Although the background properties used to find the correlation between G and oxygen saturation were quite different, the estimated oxygen concentration was accurate with a systematic error of about a few percent.

EXAMPLE 3

Figure 3:
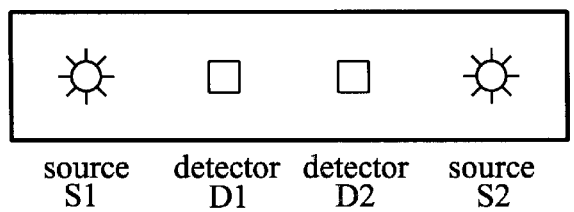
FIG. 3 is a schematic diagram of a sample optical system including two wave sources and two wave detectors arranged in a linear fashion according to the present invention.

An exemplary optical system was prepared and hemoglobin concentrations and the oxygen saturation were monitored before and after occlusion of arteries of an extremity in a human subject. FIG. 3 is a schematic diagram of a sample optical system including two wave sources and two wave detectors arranged in a linear fashion according to the present invention. Two wave detectors were linearly disposed along a straight line and separated by 6 mm. Two wave sources were disposed outside of each wave detector so that the left wave source was disposed at the left side of the left wave detector at a distance of 9 mm, and the right wave source disposed at the right side of the right wave detector at a distance of 9 mm. Accordingly, each pair of the wave sources and detectors had identical near-distances and far-distances. The wave sources had an outer diameter of 2 mm and each was designed to irradiate the electromagnetic waves having two different wavelengths. For example, laser diodes (model numbers HL6738MG and HL8325G, Thorlabs, Inc), were used to irradiate electromagnetic waves having wavelengths 690 nm and 830 nm, respectively. A photo-detector (model number OPT202 by Barr-Brown) was used as the wave detector.

A cuff was placed at the upper arm and the optical probe was disposed at the fore arm. After the subject stabilized, cuff pressure was increased to about 160 mmHg in about 35 seconds, held at the same level for about 40 seconds, and then released to atmospheric level. Concentrations of the total hemoglobin, oxygenated hemoglobin, and deoxygenated hemoglobin were monitored, along with the oxygen saturation.

Figure 4:
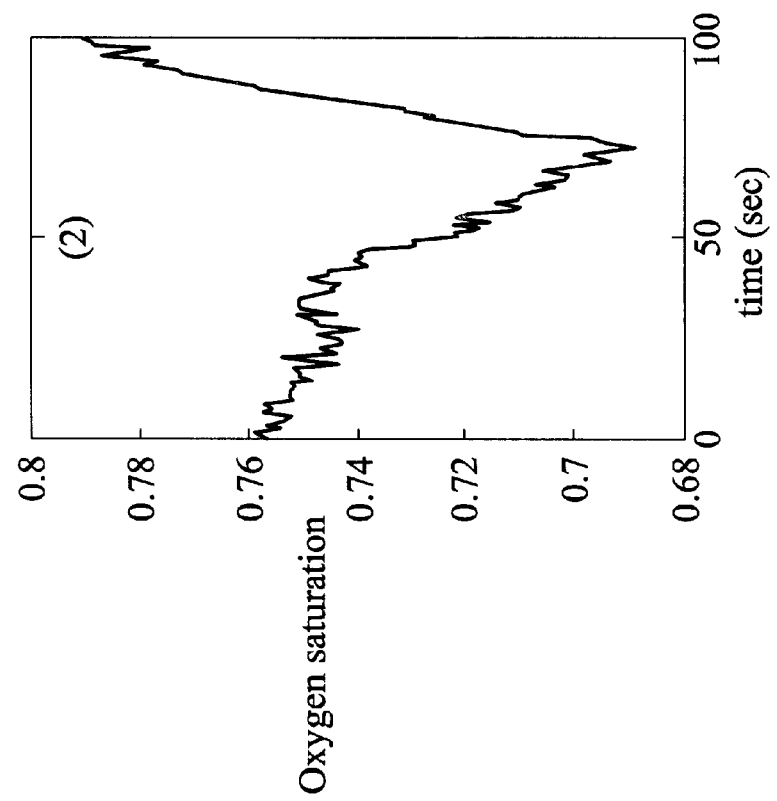
FIG. 4 is a time-course plot of total hemoglobin (HbT) concentration, oxygenated hemoglobin (HbO) concentration, and deoxygenated hemoglobin (Hb) concentration according to the present invention.
Figure 5:
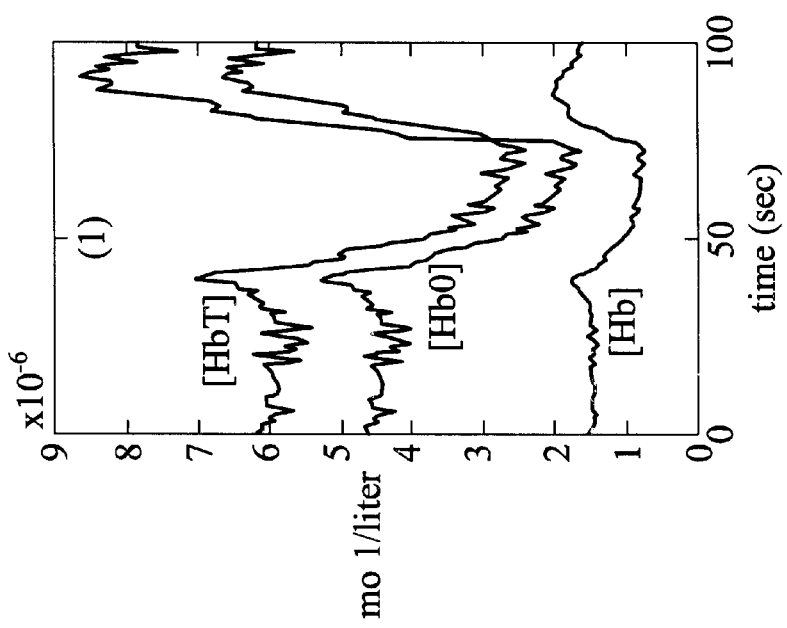
FIG. 5 is a time-course plot of oxygen saturation according to the present invention function of oxygen saturation.

FIG. 4 is a time-course plot of total hemoglobin (HbT) concentration, oxygenated hemoglobin (HbO) concentration, and deoxygenated hemoglobin (Hb) concentration according to the present invention, and FIG. 5 is a time-course plot of oxygen saturation according to the present invention. As shown in the figures, hemoglobin concentrations and oxygen saturation decreased sharply during the initial phase of occlusion, followed by a gradual decrease thereof. After the release, concentrations and oxygen saturation showed rapid increase. These results demonstrated that the optical systems and methods according to the present invention provided accurate predictions of the hemoglobin concentrations as well as the oxygen saturation. These results also showed that the optical systems possessed proper temporal response characteristics.

It is to be understood that, while various embodiments of the invention has been described in conjunction with the detailed description thereof, the foregoing is intended only to illustrate and not to limit the scope of the invention, which is defined by the scope of the appended claims. Other embodiments, aspects, advantages, and modifications are within the scope of the following claims.

What is claimed is:

1. An optical system for determining absolute values of concentrations of chromophores in a physiological medium, said optical system comprising:

a body;

a wave source configured to be supported by said body, to optically couple with said medium, and to irradiate into said medium at least two sets of electromagnetic waves having different wave characteristics;

first and second wave detectors configured to be supported by said body, to optically couple with said medium, and to detect electromagnetic waves transmitted through said medium, wherein a distance between said wave source and said first wave detector is different than a distance between said wave source and said second wave detector; and a processing module configured to operatively couple with said first and second wave detectors, and to determine an absolute value of a concentration of a chromophore in said medium from a plurality of wave equations based only on intensity measurements of continuous wave electromagnetic radiation from said first and second wave detectors.

2. An optical system according to claim 1,
wherein said chromophores are hemoglobins including oxygenated hemoglobin and deoxygenated hemoglobin.

3. An optical system according to claim 1,
wherein said physiological medium includes cells of at least one of organs, tissues, and body fluids.

4. An optical system according to claim 3,
wherein at least a portion of said cells is normal while the rest thereof is abnormal.

5. An optical system according to claim 4,
wherein said abnormal cells are tumor cells.

6. An optical system according to claim 4,
wherein said cells are disposed in at least one of epidermis, and corium of an internal organ including at least one of a brain, heart, lung, liver, and kidney.

7. An optical system according to claim 4,
wherein said cells are those of a transplanted organ.

8. An optical system according to claim 7,
wherein said transplanted organ includes at least one of a brain, heart, lung, liver, and kidney.

9. An optical system according to claim 1,
wherein said wave characteristics include at least one of wavelengths, phase angles, amplitudes, harmonics, and a combination thereof.

10. An optical system according to claim 9,
wherein a first set of said electromagnetic waves has a first wavelength and a second set of said electromagnetic waves has a second wavelength which is different from said first wavelength.

11. An optical system according to claim 9,
wherein a first set of said electromagnetic waves includes a first carrier wave and a second set of said electromagnetic waves includes a second carrier wave which has wave characteristics different from those of said first carrier wave.

12. An optical system according to claim 11,
wherein said wave characteristics include at least one of wavelengths, phase angles, amplitudes, harmonics, and a combination thereof.

13. An optical system according to claim 1,
wherein said processing module includes an algorithm configured to determine said absolute value based on an intensity of electromagnetic waves irradiated by said wave source, an intensity of electromagnetic waves detected by said first wave detector, an intensity of electromagnetic waves detected by said second wave detector, and at least one parameter accounting for an optical interaction between electromagnetic waves and said medium.

14. An optical system according to claim 13,
wherein said wave equations include at least one term substantially dependent on at least one of optical properties of said medium and configuration of said wave source and first and second wave detectors,
said algorithm including at least one correlation expressing a first function of said term as a second function of at least one of said concentrations and said ratios thereof.

15. An optical system according to claim 14,
wherein said second function is a polynomial of at least one of said concentrations and said ratios thereof.

16. An optical system according to claim 13,
wherein said wave equations include at least one term substantially dependent on at least one of optical properties of said medium and configuration of said source module and detector module,
wherein said algorithm approximates a function of said term as a constant.

17. An optical system according to claim 1,
wherein said wave equation is expressed as:

$$I = \alpha\beta\gamma I_o \exp\{-BL\delta\Sigma_i(\epsilon_i C_i) + \sigma\},$$

wherein $I_o$ is a variable for an intensity of electromagnetic waves irradiated by said wave source, I is a variable for an intensity of electromagnetic waves detected by a selected wave detector of said first and second wave detectors, $\alpha$ is a parameter associated with at least one of said wave source and medium, $\beta$ is a parameter associated with at least one of said selected wave detector and medium, $\gamma$ is one of a proportionality constant and a parameter associated with at least one of said wave source, selected wave detector, and medium, B is a parameter accounting for a length of an optical path of electromagnetic waves through said medium and associated with at least one of said wave source, selected wave detector, and medium, L is a parameter accounting for a distance between said wave source and said selected wave detector, $\delta$ is one of a proportionality constant and a parameter associated with at least one of said wave source, selected wave detector, and medium, $\epsilon_i$ is a parameter accounting for an optical interaction between electromagnetic waves and an i-th chromophore in said medium, $C_i$ is a variable denoting concentration of said i-th chromophore, and $\sigma$ is one of a proportionality constant and a parameter associated with at least one of said wave source, selected wave detector, and medium.

18. An optical system according to claim 17,
wherein said parameter B is a path length factor.

19. An optical system according to claim 17,
wherein said parameter $\epsilon_i$ is at least one of a medium extinction coefficient, medium absorption coefficient, and medium scattering coefficient.

20. An optical system according to claim 1,
further comprising another wave source.

21. An optical system according to claim 20,
wherein said wave equation is expressed as:

$$I_{mn} = \alpha_m \beta_n \gamma I_{o,m} \exp\{-B_{mn} L_{mn} \delta\Sigma_i(\epsilon_i C_i) + \sigma\},$$

wherein $I_{o,m}$ is a variable for an intensity of electromagnetic waves irradiated by an m-th wave source, $I_{mn}$ is a variable for an intensity of electromagnetic waves irradiated by said m-th wave source and detected by an n-th wave detector, $\alpha_m$ is a parameter associated with at least one of said m-th wave source and medium, $\beta_n$ is a parameter associated with at least one of said n-th wave detector and medium, $\gamma$ is one of a proportionality constant and a parameter associated with at least one of said m-th wave source, n-th wave detector, and medium, $B_{mn}$ is a parameter accounting for a length of an optical path of electromagnetic waves through said medium and associated with at least one of said m-th wave source, n-th wave detector, and medium, $L_{mn}$ is a parameter accounting for a distance between said m-th wave source and n-th wave detector, $\delta$ is one of a proportionality constant and a parameter associated with at least one of said m-th wave source, n-th wave detector, and medium, $\epsilon_i$ is a parameter accounting for an optical interaction between electromagnetic waves and an i-th chromophore included in said medium, $C_i$ is a variable denoting concentration of said i-th chromophore, and $\sigma$ is one of a proportionality constant and a parameter associated with at least one of said m-th wave source, n-th wave detector, and medium, wherein both of said subscripts m and n are non-zero positive integers.

22. An optical system according to claim 21,
wherein said parameter $B_{mn}$ is a path length factor associated with at least one of said m-th wave source, n-th wave detector, and medium.

23. An optical system according to claim 21,
wherein said parameters γ and δ are configured to be substantially close to a unity so that said wave equation is simplified as $$I_{mn} = \alpha_m \beta_n I_{o,m} \exp\{-B_{mn} L_{mn} \Sigma_i (\epsilon_i C_i) + \sigma\}.$$

24. An optical system according to claim 20,
wherein said wave sources and wave detectors configured so that a distance between said wave source and said first wave detector is substantially similar to that between said another wave source and said second wave detector, and that a distance between said first wave source and said second wave detector is substantially similar to that between said another wave source and said first wave detector.

25. An optical system according to claim 20,
further comprising at least M wave sources and at least N wave detectors wherein M and N are integers greater than 1,
said wave sources and wave detectors configured so that a distance between an $M_1$-th wave source and an $N_1$-th detector is substantially similar to that between an $M_2$-th wave source and an $N_2$-th wave detector, and that a distance between said $M_1$-th wave source and said $N_2$-th wave detector is substantially similar to that between said $M_2$-th wave source and said $N_2$-th wave detector, wherein said $M_1$ and $M_2$ are both integers between 1 and M, and wherein said $N_1$ and $N_2$ are both integers between 1 and N.

26. An optical system according to claim 20,
wherein a substantial portion of said wave detectors are disposed substantially along a straight line, at least one of said wave sources disposed on one side across said straight line and at least the other one of said wave sources disposed on the other side across said straight line.

27. An optical system according to claim 26,
wherein all of said wave detectors are disposed substantially along said straight line.

28. An optical system according to claim 20,
wherein said detector module includes at least three wave detectors each of which is disposed substantially along a straight line.

29. An optical system for determining an absolute value of concentrations of chromophores in a physiological medium, said optical system comprising:
a wave source configured to optically couple with said medium and to irradiate into said medium at least two sets of electromagnetic waves having different wave characteristics;
first and second wave detectors configured to optically couple with said medium and to detect electromagnetic waves transmitted through said medium, where a distance between said wave source and said first wave detector is different than a distance between said wave source and said second wave detector;
an equation module incorporated with a plurality of wave equations applied only to intensity measurements of continuous wave electromagnetic radiation from said first and second wave detectors; and a processing module configured to operatively couple with said first and second wave detectors and said equation module and to determine an absolute value of a concentration of a chromophore in said medium.

30. An optical system for determining an absolute value of concentrations of chromophores n a physiological medium, said optical system comprising:
at least one wave source configured to optically couple with said medium and to irradiate into said medium at least two sets of electromagnetic waves having different wave characteristics;
at least two wave detectors configured to optically couple with said medium and to detect electromagnetic waves transmitted through said medium theretoward, where one of the at least two wave detectors is at a different distance from the at least one wave source as another of the at least two wave detectors;
an equation module incorporated with a plurality of wave equations applied only to intensity measurements of continuous wave electromagnetic radiation from the at least two wave detectors; and
a processing module configured to determine an absolute value of a concentration of a chromophore in said medium based on an intensity of continuous wave electromagnetic waves irradiated by said at least one wave source, said intensity measurements of continuous wave electromagnetic radiation detected by said at least two wave detectors, and at least one parameter accounting for an optical interaction between electromagnetic waves and said medium.

31. A method of solving a set of wave equations applied to an optical system having at least one wave source and at least one wave detector wherein electromagnetic waves are irradiated by said wave source, transmitted through a physiological medium including at least one chromophore, and detected by said wave detector, said wave equation expressing an intensity of electromagnetic waves detected by said wave detector in terms of at least one variable and at least one parameter, said variable and parameter including an intensity of electromagnetic waves irradiated by said wave source, at least one source-dependent parameter accounting for an optical interaction between said wave source and medium, at least one detector-dependent parameter accounting for an optical interaction between said wave detector and medium, at least one medium-dependent parameter dependent on optical path lengths of electromagnetic waves through said medium, at least one geometry-dependent parameter dependent on configuration of said wave source and wave detector, at least one chromophore-dependent parameter accounting for an optical interaction between said chromophore and electromagnetic waves transmitted theretoward; concentration of said chromophore; and at least one auxiliary parameter which is one of a proportionality constant and a parameter depending on said wave source, wave detector, and medium, said method comprising the steps of:
obtaining a plurality of sets of equations by applying said wave equation to said optical system capable of irradiating at least two sets of electromagnetic waves having different wave characteristics;
eliminating said source-dependent and detector-dependent parameters therefrom to obtain a set of intermediate equations;
providing at least one correlation of said medium-dependent and said geometry-dependent parameter with at least one of said concentrations and said ratios thereof;

incorporating said correlation into said set of intermediate equations; and obtaining an absolute value of at least one of said concentrations and said ratios thereof based on said intensities of electromagnetic waves and said chromophore-dependent parameter.

32. A method of claim 31, wherein said wave equation is expressed as:

$$I=\alpha\beta\gamma I_o \exp\{-BL\delta\Sigma_i(\epsilon_i C_i)+\sigma\},$$

wherein $I_o$ is a variable for an intensity of electromagnetic waves irradiated by said at least one wave source, I is a variable for an intensity of electromagnetic waves detected by said at least one wave detector, $\alpha$ is a parameter associated with at least one of said at least one wave source and medium, $\beta$ is a parameter associated with at least one of said at least one wave detector and medium, $\gamma$ is one of a proportionality constant and a parameter associated with at least one of said at least one wave source, at least one wave detector, and medium, B is a parameter accounting for lengths of optical paths of electromagnetic waves through said medium and associated with at least one of said at least one wave source, at least one wave detector, and medium, L is a parameter accounting for a distance between said at least one wave source and said at least one wave detector, $\delta$ is one of a proportionality constant and a parameter associated with at least one of said at least one wave source, at least one wave detector, and medium, $\epsilon_i$ is a parameter accounting for an optical interaction between electromagnetic waves and an i-th chromophore in said medium, $C_i$ is a variable denoting concentration of said i-th chromophore, and $\sigma$ is one of a proportionality constant and a parameter associated with at least one of said at least one wave source, at least one wave detector, and medium.

33. A method of solving a set of wave equations applied to an optical system having at least one wave source and at least one wave detector wherein electromagnetic waves are irradiated by said wave source, transmitted through a physiological medium including at least one chromophore, and detected by said wave detector, said wave equation having a form:

$$I_{mn}=\alpha_m\beta_n\gamma I_{o,m} \exp\{-B_{mn}L_{mn}\delta\Sigma_i(\epsilon_i C_i)+\sigma\},$$

wherein $I_{o,m}$ is a variable representing an intensity of electromagnetic waves irradiated by an m-th wave source, $I_{mn}$ is a variable for an intensity of electromagnetic waves irradiated by said m-th wave source and detected by an n-th wave detector, $\alpha_m$ is a parameter associated with at least one of said m-th wave source and medium, $\beta_n$ is a parameter associated with at least one of said n-th wave detector and medium, $\gamma$ is one of a proportionality constant and a parameter associated with at least one of said m-th wave source, n-th wave detector, and medium, $B_{mn}$ is a parameter accounting for lengths of optical paths of electromagnetic waves through said medium and associated with at least one of said m-th wave source, n-th wave detector, and medium, $L_{mn}$ is a parameter accounting for a distance between said m-th wave source and n-th wave detector, $\delta$ is one of a proportionality constant and a parameter associated with at least one of said m-th wave source, n-th wave detector, and medium, $\epsilon_i$ is a parameter accounting for an optical interaction between electromagnetic waves and an i-th chromophore in said medium, $C_i$ is a variable for concentration of said i-th chromophore, and $\sigma$ is one of a proportionality constant and a parameter associated with at least one of said m-th wave source, n-th wave detector, and medium, said method comprising the steps of:

obtaining a first and a second set of equations by applying said wave equation to said optical system capable of irradiating a first and second set of electromagnetic waves having different wave characteristics, respectively;

eliminating at least one of $\alpha_m$, $\beta_n$, $\gamma$, $\delta$, and $\sigma$ from said first and second set of equations by performing mathematical operations thereon to obtain a third set of equations;

providing at least one correlation of at least one of said concentrations and said ratios thereof with at least one term of said third set of equations including at least one of $B_{mn}$ and $L_{mn}$;

incorporating said correlation into said third set of equations to eliminate said term therefrom; and obtaining an expression for an absolute value of at least one of said concentrations and said ratios thereof based on said $I_{mn}$, $I_{o,m}$, and $\epsilon_i$.

34. A method of claim 33 further comprising the steps of:

applying said optical system to said physiological medium including cells of at least one of organs, tissues, and body fluids; and measuring said absolute value of at least one of said concentrations and said ratios thereof based on said $I_{mn}$, $I_{o,m}$, and $\epsilon_i$.

35. A method of claim 34, wherein said measuring step comprises the step of:

monitoring at least one of oxygenated hemoglobin concentration, deoxygenated hemoglobin concentration, and a ratio thereof.

36. A method of claim 35 further comprising the step of:

determining a presence of tumor cells over a finite area of said medium.

37. A method of claim 35 further comprising the step of:

determining a presence of an ischemic condition over a finite area of said medium.

38. A method of claim 33 further comprising the steps of:

applying said optical system to said physiological medium including transplanted cells of at least one of organs and tissues; and measuring said absolute value of at least one of said concentrations and said ratios thereof based on said $I_{mn}$, $I_{o,m}$, and $\epsilon_i$.

39. A method of claim 38 further comprising the step of:

determining a presence of an ischemic condition over a finite area of said medium.

40. A method of claim 33, wherein said eliminating step comprises the step of:

approximating said parameters g and d as a unity.

41. A method of claim 33, wherein said obtaining step comprises the step of:

irradiating said first and second set of electromagnetic waves having at least one of different wavelengths, phase angles, amplitudes, harmonics, and a combination thereof.

42. A method according to claim 41, wherein said irradiating step comprises the steps of:

providing said first set of electromagnetic waves with a first wavelength; and providing said second set of electromagnetic waves with a second wavelength which is different from said first wavelength.

43. A method of claim 33, wherein said eliminating step comprises the step of:

taking at least one first ratio of two wave equations both selected from one of said first and second sets of wave equations.

44. A method of claim 43, wherein said eliminating step comprises the step of:
applying said wave equations to the same wave source but to different wave detectors, thereby eliminating $\alpha_n$, $\gamma$, and $\sigma$ from said first ratio.

45. A method of claim 43, wherein said eliminating step comprises the step of:
applying said wave equations to two different wave sources but to the same wave detector, thereby eliminating $\beta_n$, $\gamma$, and $\sigma$ from said first ratio.

46. A method of claim 43, wherein said eliminating step comprises the step of:
taking at least one second ratio of two wave equations both selected from the other of said first and second sets of wave equations.

47. A method of claim 46, wherein said eliminating step comprises the step of:
obtaining at least one of a sum of and a difference between said first and second ratios so as to eliminate at least one of $\alpha_m$ and $\beta_n$ therefrom.

48. A method of claim 33, wherein said providing step comprises the step of:
expressing a formula of said medium-dependent and said geometry-dependent parameters as a polynomial of at least one of said concentrations and said ratios thereof.

49. A method of claim 48, wherein said polynomial includes a zero-th order term.

50. A method of claim 33, wherein said providing step comprises the step of:
expressing a formula of said medium-dependent and said geometry-dependent parameters as a constant.

51. A method of solving a set of wave equations applied to an optical system having at least one wave source and at least one wave detector wherein electromagnetic waves are irradiated by said wave source, travel through a physiological medium including at least one chromophore, and detected by said wave detector, said wave equation having a form:

$$I_{mn}=\alpha_m\beta_n\gamma I_{o,m}\exp\{-B_{mn}L_{mn}\delta\Sigma_i(\epsilon_i C_i)+\sigma\},$$

wherein $I_{o,m}$ is a variable representing an intensity of electromagnetic waves irradiated by an m-th wave source, $I_{mn}$ is a variable for an intensity of electromagnetic waves irradiated by said m-th wave source and detected by an n-th wave detector, $\alpha_m$ is a parameter associated with at least one of said m-th wave source and medium, $\beta_n$ is a parameter associated with at least one of said n-th wave detector and medium, $\gamma$ is one of a proportionality constant and a parameter associated with at least one of said m-th wave source, n-th wave detector, and medium, $B_{mn}$ is a parameter accounting for lengths of optical paths of electromagnetic waves through said medium and associated with at least one of said m-th wave source, n-th wave detector, and medium, $L_{mn}$ is a parameter accounting for a distance between said m-th wave source and n-th wave detector, $\delta$ is a one of a proportionality constant and a parameter associated with at least one of said m-th wave source, n-th wave detector, and medium, $\epsilon_i$ is a parameter accounting for an optical interaction between electromagnetic waves and an i-th chromophore in said medium, $C_i$ is a variable for concentration of said i-th chromophore, and $\sigma$ is one of a proportionality constant and a parameter associated with at least one of said m-th source, n-th detector, and medium, said method comprising the steps of:
obtaining a first set of wave equations by applying said wave equation to said optical system including at least one of said wave source configured to irradiate electromagnetic waves having a first wave characteristics;
obtaining a second set of wave equations by applying said wave equation to said optical system including at least the other one of said wave source configured to irradiate electromagnetic waves having a second wave characteristics;
eliminating at least one of $\alpha_m$, $\beta_n$, $\gamma$, $\delta$, and $\sigma$ from said first and second sets of wave equations so as to obtain a third set of equations;
deriving at least one formula expressing said parameters including $B_{mn}$ and $L_{mn}$ as a function of at least one of said concentrations and said ratio of concentrations; and
incorporating said formula into said third set of equations to eliminate $B_{mn}$ and $L_{mn}$.

52. A method of claim 51 further comprising the steps of:
obtaining values of said intensities of electromagnetic waves and said extinction coefficients of said chromophores; and
incorporating said intensities of electromagnetic waves and extinction coefficients into said third set of equations.

53. A method of claim 52 further comprising the steps of:
obtaining an expression for an absolute value of at least one of said concentrations and said ratios thereof.

* * * * *